United States Patent [19]
Janda et al.

[11] Patent Number: 5,563,121
[45] Date of Patent: Oct. 8, 1996

[54] PEPTIDE LINKAGE UNIT

[75] Inventors: Kim D. Janda, San Diego; Peter Wirsching, Solana Beach; Shoji Ikeda, San Diego, all of Calif.

[73] Assignee: The Scripps Research Institute, La Jolla, Calif.

[21] Appl. No.: 256,236

[22] PCT Filed: Jan. 11, 1993

[86] PCT No.: PCT/US93/00228

§ 371 Date: Jun. 30, 1994

§ 102(e) Date: Jun. 30, 1994

[87] PCT Pub. No.: WO93/00228

PCT Pub. Date: Jan. 11, 1993

[51] Int. Cl.$^6$ .............. A61K 38/03; C07K 4/00; C07K 5/02; C07K 7/02
[52] U.S. Cl. .............. 514/7; 530/323; 530/326; 530/327; 530/328; 530/329; 530/330; 562/17; 562/18; 930/30
[58] Field of Search .............. 514/2, 14, 15, 514/16, 17, 18, 7; 930/21, 30; 530/323, 326, 327, 328, 329, 330, 331, 332; 562/17, 18

[56] References Cited

U.S. PATENT DOCUMENTS 4,148,624  4/1979  Maier ..................... 504/175

OTHER PUBLICATIONS

Bartlett, et al., "Potent Inhibition of Pepsin and Pepicillo–Pepsin by Phosphorus–Containing Peptide Analogs", *J. Org. Chem.*, 55:6268–6274 (1990).

Huff, et al., "HIV Protease: A Novel Chemotherapeutic Target for AIDS", *J. Med. Chem*, 34: 2305–2314 (1991).

*Primary Examiner*—Jeffrey E. Russel
*Attorney, Agent, or Firm*—Donald G. Lewis

[57] ABSTRACT

A peptide linkage unit is employed for joining peptide and pseudopeptide sequences, including peptides and pseudopeptides that inhibit aspartic proteinase enzymes. The peptide linkage unit includes a phosphinate methylene ammonium linkage in place of a peptidyl carboxamide bond. If the peptide linkage unit is incorporated into a peptide sequence that would otherwise serve as an aspartic proteinase substrate and if it is positioned at a cleavage site within such peptide sequence, the phosphinate methylene ammonium linkage is resistant to cleavage and serves as an exploding transition state analog of such cleavage site. When so incorporated, the phosphinate methylene ammonium linkage can bind or interfere with the active site of aspartic proteinase enzymes and inhibit its activity. Preferred inhibitors contain a phosphinic acid methylene amine group joining the $P_1$ and $P_1'$ residues and have a length of 3 to about 15 amino acid residues.

44 Claims, No Drawings

PEPTIDE LINKAGE UNIT

DESCRIPTION

1. Technical Field

The present invention relates to linkage units for joining peptide sequences and to the use of such linkage units for forming peptides and pseudopeptides, including pseudopeptides that inhibit aspartic proteinase enzymes. More particularly, the invention relates to pseudopeptides that include a phosphinate methylene ammonium linkage (exploding transition state analog) in place of an amide bond at the position in a peptide sequence that is cleaved by aspartic proteinase enzymes.

2. Background Art

Peptide linkage units are employed in the construction of peptides. In the simplest case, naturally occurring L-amino acids serve as peptide linkage units. However, various unnatural L-amino acids and a wide variety of D-amino acids may also serve as peptide linkage units. The peptide linkage unit need not employ a peptide bond to form the linkage. A number of pseudopeptides are disclosed and employed in the prior art as peptide linkage units.

A peptide linkage unit may be employed to link two peptide sequences or may be employed at the terminal end of a peptide. The peptides lying on either side of a peptide linkage unit may be functionally distinct.

Peptide linkage units are employed in the construction of synthetic proteinase inhibitors. Many proteinase substrates include a proteinase binding or recognition region which flanks either side of the cleavage site. Accordingly, one class of synthetic proteinase inhibitor employs peptides having amino acid sequence homology with the binding or recognition regions of known proteinase substrates. If two such peptides are employed in a synthetic proteinase inhibitor, i.e. peptides having a sequence homology with the binding or recognition region flanking either side of a cleavage site, a peptide linkage unit may then be employed to link the two peptides together. In this instance, the peptide linkage unit will be positioned at or near the cleavage site. Peptide linkage units which are resistant to proteolysis and which bind tightly to the active site of the proteinase are particularly useful in the construction of synthetic proteinase inhibitors.

Aspartic proteinase enzymes (EC 3.4.23) are a family of related enzymes that cleave (hydrolyze) protein and polypeptide chains. These enzymes have isoelectric points on the acid side of neutrality and molecule masses ranging from 35,000–45,000 Daltons (D) for fungal enzymes and about 35,500 D for pepsin.

Exemplary enzymes of this class include pepsin that is a mammalian gastric proteinase, cathepsin D that is the intracellular aspartic proteinase of the lysosomal system and whose level has been positively correlated with recurring breast cancers [Tandon et al., *N. Eng. J. Med.*, 322:297 (1990)] and with amyloid formation in Alzheimer's plagues [Cataldo et al., *Brain Res.*, 513:181 (1991)], renin that regulates blood pressure by its cleavage of angiotensinogen to form angiotensin I, and chymosin (formerly called rennin) that cleaves milk proteins as a first step in cheese making. Penicillopepsin, a microbial enzyme from *P. janthinellum* is another member of this family, whereas nepenthesin, the digestive proteinase of the pitcher plant is exemplary of the plant aspartic proteinases.

The HIV-1 virus also contains an aspartic protease. That enzyme is known to cleave the p17–p24 region of the Pr55$^{gag}$ fusion protein. Moore et al., *Biochem, Biophys. Res. Comm.*, 159:420 (1989).

Although the precise mechanism of action of this family of enzymes is not as well known as that of the serine proteinases, it is believed that two aspartic acid groups act with water in the active site to cause hydrolysis of the peptide bond that is hydrolyzed. The hydrolyzed peptide bond is typically between hydrophobic residues. A covalent intermediate is not thought to be formed between this enzyme and its substrate as is the case with the serine proteinase family.

This family of enzymes forms an enzyme-substrate complex as is typical in enzyme-substrate reactions. Binding is often found to be a two-step process even though no covalent bonds are formed.

Several peptide and peptidomimetic compounds have been reported in the literature that inhibit the action of aspartic proteinases. Exemplary discussions of such inhibitors are found in Rich, *Proteinase Inhibitors*, Chapter 5, Volume 12, Barrett and Salveson eds., Dingle and Gordon general eds., Elsevier Science Publishers BV, Amsterdam (1986), and Rich, *Peptide Inhibitors, Comprehensive Medicinal Chemistry*, Chapter 8.2, Sammes, ed., Pergamon Press, Oxford, Volume 2 (1990).

Several inhibitors include polypeptides similar in sequence to a natural substrate of an enzyme that also include one or more D-amino acids in place of the naturally occurring L-amino acids. Another group of inhibitors contains the surrogate (3S,4R)-4-amino-3-hydroxy-6-methyl-heptanoic acid, designated AHMHA or statine (Sta), in place of the two residues between which the hydrolysis occurs, such as Leu and Ala. The statine-containing group of inhibitors were first found in the naturally occurring inhibitor known as pepstatin A that inhibits each of pepsin cathepsin D with a $K_i$ value of about $10^{-10}$–$10^{-11}$M and renin with a $K_i$ value of $10^{-6}$M.

Inhibitors containing a hydroxyethylamine moiety as a peptide bond surrogate have also been reported. Inhibitors of particular interest herein that contain the hydroxyethylamine surrogate bond have been reported in Roberts et al., *Science*, 248:358 (1990), Krohn et al., *J. Med. Chem.* 34:3740 (1991) and Rich et al., J. Med. Chem., 34:1222 (1991). A review discussing results for several HIV-related aspartic proteinase inhibitors is found in Huff, *J. Med. Chem.*, 34:2305 (1991).

Yet another group of inhibitors, reported in Luby et al., *J. Med. Chem.*, 31:532 (1988), utilized an oligopeptide analog of angiotensinogen in which the cleavable Leu-Val dipeptide was replaced with an iso-propylsulfidoethanol derivative surrogate. Roberts et al., *J. Med. Chem.*, 33:2326 (1990) reported using 1,2,4-triazolo[4,3-a]pyrazine derivatives as surrogates to replace the amino-terminal three residues adjacent to the leucine of the cleaved angiotensinogen Leu-Val bond in renin inhibitory molecules.

In another recent paper, [Bartlett et al., *J. Org. Chem.*, 55:6268 (1990)] phosphonate-, phosphinate- and phosphinamide-containing pseudopeptide inhibitors of pepsin and penicillopepsin were reported. Those inhibitors were pseudopeptides that included a phosphorus-containing bond in place of the scissile amide bond that would normally be cleaved by those enzymes.

A phosphonate group has the linkage —P(O)(OH)O—, in which the shown valence of the phosphorus atom is bonded to a carbon and takes the place of an amide carbonyl group, and the free valence of the oxygen is bonded to a carbon atom, taking the place of the amido —NH— group. A phosphinate group has the linkage —P(O)(OH)—, so that the phosphorus atom is bonded to two carbon atoms. A phosphinamide has the linkage —P(O)(NH$_2$)—, so that the phosphorus atom is bonded to two carbon atoms and includes an —NH$_2$ side group.

As can be seen from the above linkages, the phosphonate- and phosphinate-containing compounds having pK$_a$ values of about 1.5 and 3.0, respectively, would be expected to bear an anionic charge at physiological pH values, e.g. pH 7.2–7.4. Bartlett et al., above, also disclosed preparation of compounds containing a phosphonate ester linkage [—P(O)(OCH$_3$)O—] as intermediates in the preparation of the phosphonate derivatives, but reported no inhibition data using those esters that were cleaved to form the assayed phosphonates.

BRIEF SUMMARY OF THE INVENTION

The present invention contemplates a linkage unit for joining two peptide sequences, i.e. an amino terminal peptide sequence and a carboxyl terminal peptide sequence. In a preferred embodiment, the linkage unit comprising a dipeptide having a first amino acid residue (aa$_1$), a second amino acid residue (aa$_2$), and an "exploded" linkage between the first and second amino acid residues. The first amino acid residue is conventional except that it lacks a backbone carbonyl group and has, instead, a phosphinic acid group, i.e. (aa$_1$—POOH—). The second amino acid residue is also conventional and includes a backbone amino group, i.e. (—NR—aa$_2$), where R is H or C. The exploded linkage between the first and said second amino acid residues lacks but has, instead, a methylene group. The methylene group is bonded both to the phosphinic acid group of the first amino acid residue and to the backbone amino group of the second amino acid residue. The resultant phosphinic acid methylene amino bonds form an "exploded" linkage.

At acid pH, this "exploded" linkage can be represented by the following formula, viz.:

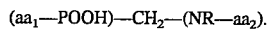

(aa$_1$—POOH)—CH$_2$—(NR—aa$_2$).

At or near physiological pH, the phosphinic acid and amino groups are to zwitterionic phosphinate and ammonium groups. In this instance the "exploded" linkage can be represented by the following formula, viz.:

(aa$_1$—POO$^-$)—CH$_2$—(NHR$^+$—aa$_2$).

The above dipeptide constitutes a linkage unit which can be employed to link amino acid residues or sequences. The first amino acid residue (aa$_1$) within the dipeptide may include a bondable amino group which can be employed to form a peptide linkage with the carboxyl group of a "flanking" amino acid or with the carboxyl group of an amino terminal peptide sequence. In addition or alternatively, the second amino acid residue (aa$_2$) within the dipeptide may include a bondable carboxyl group which can be employed to form a peptide linkage with the amino group of a "flanking" amino acid or with the amino group of a carboxyl terminal peptide sequence. The resultant oliogo or polypeptide is improved because it includes the linkage unit with its dipeptide having an "exploded" methylene linkage. The "exploded" methylene linkage may be positioned between two-peptide sequences, i.e. the amino terminal and carboxyl terminal peptide sequences, or may be attached to only one of these sequences.

The present invention also contemplates an inhibitor for an aspartic proteinase enzyme. The inhibitor is a pseudopeptide that includes a phosphinic acid methylene amine linkage [PO(OH)CH$_2$NH$_a$], usually present in zwitterionic form as a phosphinate methylene ammonium linkage (PO$_2^-$ $CH_2NH_a^+$), in place of the peptidyl amide bond at the position in the pseudopeptide sequence that is cleaved by the enzyme, "a" being zero, one or two. That new linkage is sometimes referred to herein as an exploding transition state analog. Thus, an oligopeptide having a peptide bond at the position occupied by the phosphinate methylene ammonium linkage of an inhibitor of the invention is cleaved by an aspartic proteinase.

A pseudopeptide aspartic proteinase inhibitor typically has a length of 3 to about 15 amino acid residues, preferably 4 to about 10 residues, and contains a P$_1$ to P$_1$' bond that is constituted by a phosphinate methylene ammonium linkage in which the phosphorus atom is bonded to P$_1$ in place of the carbonyl carbon atom and methylene amine replaces the amide nitrogen of a peptide bond.

A particularly preferred pseudopeptide of the invention can be represented by the zwitterionic formula

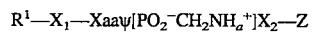

R$^1$—X$_1$—Xaaψ[PO$_2^-$CH$_2$NH$_a^+$]X$_2$—Z wherein X$_1$, is an amino acid residue or oligopeptide containing a sequence of up to about ten amino acid residues;

a is zero, one or two so that zero, one or two hydrogens are present, respectively;

Xaa is a surrogate amino acid residue having an amino acid side chain;

X$_2$ is an amino acid residue or oligopeptide containing a sequence of up to about ten amino acid residues;

Z is selected from the group consisting of NH$_2$, NH—C$_1$–C$_6$ acyl, OH, O—C$_1$–C$_6$ alkyl, NH—C$_1$–C$_6$ alkyl and 2-amidoindanol; and R$^1$ is selected from the group consisting of hydrogen, C$_1$–C$_6$ acyl, trifluoroacetyl, quinolin-2-ylcarbonyl and t-BOC.

A pseudopeptide preferably competitively inhibits the in vitro activity of an aspartyl proteinase with an inhibition constant of about 10$^{-6}$ to about 10$^{-11}$M, and more preferably about 10hu −8 to about 10$^{-11}$M.

In preferred practice, Xaa has the side chain of a Leu, Tyr or Phe residue, and the amino-terminal residue of X$_2$ is Tyr, Leu, Val, Met, Pro, Ala or Phe. X$_2$ can also be a piperidine-2(s)carboxyl group (PIC) or a (4aS,8aS)-decahydroisoquinoline-3(S)carboxyl group (DIQ), or an amide or ester thereof.

A pharmaceutical composition that contains an above pseudopeptide in an amount sufficient to inhibit an aspartic proteinase dissolved or dispersed in a physiologically tolerable carrier or diluent is also contemplated.

Further contemplated is a method for inhibiting an aspartic proteinase. Here, an above composition is admixed in an aqueous medium with the enzyme and a substrate for the enzyme to form an inhibition mixture. The inhibition mixture so formed is maintained for a time sufficient for the aspartic proteinase activity of the enzyme to be inhibited.

Definitions

A compound of the invention is depicted using the "psi bracket" (ψ[]) nomenclature for oligopeptide analogs having backbone modification described in Spatola, *Chemistry and Biochemistry of: Amino Acids, Peptides and Proteins*, Weinstein, ed., Volume 7, chapter 5, Marcel Dekker, Inc., New York, pages 267–357 (1983). In accordance with that nomenclature:

(a) hyphens between amino acid residues indicate the presence of a peptide bond joining the residues;

(b) absence of a hyphen, combined with the symbol ψ (psi) indicates the removal of the amide peptide bond elements leaving the α-carbon and its side chain; p1 (c) the presence of brackets, [], adjacent the ψ symbol and between residues, coupled with a structural group within the brackets indicates that the specified structural group within the brackets replaces the peptidyl amide bond;

(d) the word "surrogate" refers to an unnatural replacement for a naturally occurring entity, so that a psi-bracketed structural group is a surrogate for the peptidyl amide bond as is the residue containing the bond surrogate a surrogate for an amino acid residue;

(e) the term "pseudopeptide" refers to a peptide analog having a peptide backbone modification;

(f) a "pseudodipeptide" is a modified dipeptide structural unit that contains a surrogate bond(s) or amino acid residue(s); and (g) hyphens at pseudopeptide termini, not being part of the pseudopeptide backbone, merely refer to bonds.

A compound of this invention contains a $PO(OH)CH_2$ group in place of a petidyl amide carbonyl group. Such a compund thus contains a pentavalent, tetrahedral phosphorus atom as part of a phosphinic acid methylene amine that is written $\psi[PO(OH)CH_2NH_a]$ as a surrogate for a peptidyl amide bond. That linkage is written $\psi[PO_2^-CH_2NH_a^+]$ as a phosphinate methylene ammonium in zwitterionic form. The linkage can also exist as $\psi[PO_2HCH_2NH^+]$, $\psi[PO(OH)CH_2NH_2^+]$, $\psi[PO_2^-CH_2N]$ and the like depending upon pH values and the amino acid residue of $P_1'$, as discussed hereinafter Inasmuch as a contemplated oligopseudopeptide is usually present in zwitterionic form, the peptidyl amide bond surrogate is usually referred to as a phosphinate methylene ammonium group or linkage.

The term "oligopeptide" is used in its usual sense to mean a peptide containing ten or fewer amino acid residues. Similarly, the term "oligopseudopeptide" refers to a pseudopeptide containing ten or fewer amino acid residues and surrogates therefor.

Another nomenclature system used herein is that of Schechter and Berger, *Biochem. Biphys. Res. Commun.*, 27:157 (1967) that was developed for describing peptide substrates for hydrolase enzymes. In accordance with that nomenclature system, a peptide substrate for a hydrolase enzyme is numbered in two directions from the point of hydrolytic cleavage. The amino acid residues of the dipeptide portion that is cleaved are numbered $P_1$ and $P_1'$ such that after cleavage, the $P_1$ residue becomes the carboxy-terminal residue of one cleaved portion and the $P_1'$ residue becomes the amino-terminal residue of the other portion. The remaining residues toward the carboxy-terminus of the $P_1'$-containing portion are numbered $P_2'$, $P_3'$, $P_4'$. . . and so on toward the carboxy-terminus. The remaining residues of the portion containing the $P_1$ residue are numbered toward the amino-terminus of that portion as $P_2$, $P_3$, $P_4$. . . and so on.

The dipeptide portion of a hydrolase substrate oligopeptide that is cleaved is thus defined as $P_1$-$P_1'$. The Schechter and Berger nomenclature system is utilized whether or not the bond linking the $P_1$ and $P_1'$ residues is a peptide bond or is capable of hydrolytic cleavage, and is therefore useful with pseudopeptides where $P_1$-$P_1'$ constitutes the before-defined pseudodipeptide that is not cleaved.

The Schechter and Berger nomenclature system therefore not only identifies the bond normally cleaved, but also identifies the positions of residues on either side thereof regardless of whether the compound is an oligopeptide or a pseudopeptide. Following that nomenclature, residues $P_1$ and $P_1'$ of a contemplated pseudopeptide described hereinafter are joined by the phosphinate methylene ammonium group.

DETAILED DESCRIPTION OF THE INVENTION

I. Background

The present invention relates to pseudopeptide compounds that reversibly bind to and competitively inhibit the activity of an aspartic proteinase. A contemplated oligopeptide analog inhibits that enzymatic activity in the presence of a substrate for the enzyme and is therefore a competitive inhibitor.

A compound contemplated herein is referred to as a pseudopeptide because although most of the subunit amino acids are linked by peptidyl amide bonds, two such residues are linked by a peptidyl amide bond surrogate phosphinic acid methlene amine group (phosphinate methylene ammonium group as a zwitterion). The peptidyl amide bond surrogate is often referred to by the zwitterionic name. Compounds containing peptide bonds and other bonds linking moieties having amino acid side chains are also sometimes referred to as peptidomimetic compounds.

A contemplated pseudopeptide reversibly binds to an aspartic proteinase to form an enzyme-inhibitor complex. Such binding and complex formation are familiar to those skilled in enzyme kinetics, and are to be distinguished from the interactions of materials that irreversibly bind to and react with an enzyme that are sometimes referred to as "suicide inhibitors". Thus, a contemplated pseudopeptide binds to (or is bound by) an aspartic proteinase, but does not chemically react with the enzyme.

Phosphonamidate-containing compounds have been used as transition state analog inhibitors for metallopeptidases such as carboxypeptidase A, thermolysin and angiotensin converting enzyme (ACE). See, for example Rich, *Peptidase Inhibitors. Comprehensive Medicinal Chemistry*, Chapter 8.2, Sammes, ed., Pergamon Press, Oxford, Volume 2 (1990). In addition, a number of phosphonamidate S- and O- esters have been investigated as irreversible phosphorylating agents of serine proteinases. See, for example, Sampson et al., *Biochem*, 30:2255 (1991); Oleksyszyn et al., *Biochem. Biophys Res, Comm.*, 161:143 (1989); and Pratt, *Science*, 246:917 (1989); and Bartlett et al., Bioorg. Chem, 14:356 (1986).

Metallopeptidases and serine proteinases act on their substrates in a different manner than do aspartic proteinases. In addition, the non-esterified phosphonamidates are unstable under the acid pH conditions at which aspartic proteinase enzymes typically act and are therefore poor candidates for use in inhibitors. The exploding transition state analog-containing pseudopeptides contemplated herein are stable at the acidic pH values at which aspartic proteinases act.

One strategy utilized in preparing aspartic proteinase inhibitors is to replace the scissile $P_1$-$P_1'$ peptide bond with a non-hydrolyzable bond surrogate that is an isostere for the tetrahedral carbon atom of the transition state for amide bond hydrolysis. The previously noted phosphinic and phosphonic acid pseudopeptide derivatives described in Bartlett et al., *J. Org. Chem.*, 55:6268 (1990) and statine group of pepstatin A fulfill that function.

A phosphinate methylene ammonium linkage of a compound described herein also can be viewed as an isostere of an amide hydrolysis transition state. It is thought that the phosphinate methylene ammonium linkage represents an isostere for the late transition state of amide hydrolysis; i.e., an isostere to the hydrated enzyme-bound substrate whose carbonyl group/nitrogen atom bond is stretched almost to breaking and whose hydrated carbonyl group and nitrogen atom bear developing charges.

Structural features of a phosphinate methylene ammonium linkage include: (a) positive and negative charges that mimic the developing charges for the hydrolysis of a peptide bond; (b) the phosphinate portion is an excellent representation of the acyl carbon that becomes tetrahedral in the hydrated transition state; (c) the methylene unit acts as a spacer separating the two charged heteroatoms by about 2.2 Å, thus providing the "explosion" of the analog amide bond moiety; (d) this peptide bond surrogate is both acid and base stable as compared to phosphonate and phosphonamidate; and (e) the zwitterionic character at physiological pH values; i.e. about pH 7.2–7.4, promotes water solubility of the pseudopeptide. A phosphinate methylene ammonium group contemplated herein as a zwitterion is also electrically neutral (is free from net ionic charge) at pH values encountered in living organisms and as such contributes to passage of a pseudopeptide through cell membranes.

II. The Pseudopeptides

A contemplated preferred pseudopeptide aspartic proteinase inhibitor can have a length of 3 to about 15, and more preferably 4 to about 10, amino acid residues and has a $P_1$ to $P_1'$ bond surrogate that is constituted by a phosphinate methylene ammonium linkage (group) in which the phosphorus atom is bonded to (i) a carbon at $P_1$ in place of the carbonyl carbon atom of a peptide bond, and (ii) a methylene ammonium group (as a zwitterion) in place of the amido nitrogen atom of a peptide bond.

Such an inhibitor typically inhibits the in vitro activity of an aspartic proteinase with an inhibition constant, $K_i$, of about $10^{-6}$ to about $10^{-11}$M. The inhibition constant is readily ascertained in the presence of a usual, native substrate for the enzyme as discussed hereinafter.

The residue length of a contemplated inhibitor is determined as if the $P_1$–$P_1'$ positions were linked by a peptide bond. The $P_1$ position surrogate residue is thus considered for this purpose to be an amino acid residue even though the carboxyl group normally present is replaced by a tetrahedral phosphorus-containing moiety.

A particularly preferred contemplated pseudopeptide has the formula

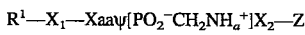

$$R^1-X_1-Xaa\psi[PO_2^-CH_2NH_a^+]X_2-Z$$

wherein $X_1$ is an amino acid residue or oligopeptide containing a sequence of up to about ten amino acid residues;

a is zero, one or two;

Xaa is a surrogate amino acid residue having an amino acid side chain;

$X_2$ is an amino acid residue or oligopeptide containing a sequence of up to about ten amino acid residues;

Z is selected from the group consisting of $NH_2$, NH—$C_1$–$C_6$ acyl, OH, O—$C_1$–$C_6$ alkyl, NH—$C_1$–$C_6$ alkyl and 2-amidoindanol; and $R^1$ is selected from the group consisting of hydrogen, $C_1$–$C_6$ acyl, trifluoroacetyl, quinolin-2-ylcarbonyl and t-BOC.

The subscript "a" adjacent to the hydrogen in the phosphinate methylene ammonium linkage surrogate peptide bond indicates the number of hydrogens (protons) present, and can be zero, one or two (0, 1 or 2) depending upon pH value and the $P_1'$ residue, as noted previously. The nitrogen atom of that surrogate is present as an amine rather than as an amide, and consequently can be protonated at physiological pH values and lower pH values where an amide nitrogen atom is normally not protonated. That ammonium group can also be deprotonated and a free amine at higher pH values.

All of the α-amino groups of the naturally occurring amino acids are primary amines that contain two hydrogen atoms, except for that of proline (Pro) that is a secondary amine and contains one hydrogen atom. Thus, "a" for the naturally occurring amino acid residues other than proline is one in unprotonated (free amine) form and two in protonated (ammonium) form. For proline, "a" is zero in unprotonated form and one in protonated form. The two unusual amino acids PIC and DIQ (described hereinafter) are also secondary amines so that "a" is zero or one for an oligopseudopeptide containing PIC of DIQ. The amino group of the surrogate bond is usually depicted as protonated herein in view of the basicity of the amino group of the surrogate, and so "a" is usually one or two.

In view of the before-discussed relative low $pK_a$ value of the phosphinate group, the phosphinate-containing portion of the surrogate bond is normally deprotonated in aqueous solution at physiological pH values and those slightly acidic pH values at which aspartic proteinases usually function. That portion is thus illustrated as $PO_2^-$.

The surrogate phosphinate methylene ammonium linkage is therefore sometimes shown herein as a zwitterion in which the phosphinate is deprotonated and negatively charged, and the amine is shown as protonated and positively charged. The zwitterionic and unionized forms are to be taken as equivalent. It is to be understood, however, that protonation of the phosphinate and amino portions can vary with the pH value of a medium in which a pseudopeptide is present, or from which it was obtained.

A particularly preferred pseudopeptide has a length of 4 to about 10 amino acid residues, and competitively inhibits the in vitro activity of the aspartyl proteinase with an inhibition constant of about $10^{-8}$ to about $10^{-11}$M.

Exemplary $C_1$–$C_6$ acyl groups of $R^1$ and Z include formyl, acetyl, propionyl, butanoyl, iso-butanoyl, isovaleryl (Iva), hexanoyl, cyclopentylcarbonyl and the like. A t-BOC group is a tertiary-butyloxy carbonyl group as is often used as a protecting group in solid phase peptide syntheses, and is utilized herein bonded to an amino-terminal amine or ε-amino group of a lysine residue. An N-terminal quinolin-2-ylcarbonyl (QC) group is also contemplated. Exemplary $C_1$–$C_6$ alkyl groups of Z include methyl, ethyl, propyl, iso-propyl, butyl, iso-butyl, sec-butyl tert-butyl (t-butyl; tertiary-butyl or $^t$Bu) pentyl, 2-methylbutyl, cyclopentyl, hexyl, cyclohexyl, and the like, so that the pseudopeptide is present as a carboxy-terminal $C_1$–$C_6$ alkyl ester.

The group Xaa is a surrogate amino acid residue having the side chain of an amino acid. Although Xaa can have any side chain of one of the twenty naturally occurring amino acids, Xaa preferably has the side chain of a Leu, Tyr or Phe amino acids. The Xaa group is in the $P_1$ position of a contemplated pseudopeptide.

Each of $X_1$ and $X_2$ can be an amino acid residue or an oligopeptide of up to about ten, and preferably up to about five amino acid residues. The sequences of $X_1$ and $X_2$ can contain any amino acid residues. Preferably, the amino-terminal residue of X2 (the $P_1'$ position residue) is selected from the group consisting of Tyr, Leu, Val, Met, Pro, Ala and Phe. $X_2$ can also be a piperidine-2(s)carboxyl group (PIC) or a (4aS,8aS)-decahydroisoquinoline-3(S)carboxyl group (DIQ). These $X_2$ moieties can be viewed as analogs of proline. 10 The overall length of a pseudopeptide, aside from an $R^1$ or Z group, is 3 to about 15 amino acid residues, and more preferably 4 to about 10 amino acid residues. Thus, although each of $X_1$ and $X_2$ can separately be up to about 10 amino acid residues in length, both cannot include 10 amino acid residues.

Nevertheless, $X_1$ can include 10 amino acid residues (occupying positions $P_2$–$P_{11}$ of the sequence) and $X_2$ can include four residues (occupying positions $P_1'$–$P_4'$ of the sequence). $X_2$ can similarly include 10 residues with $X_1$ including 4 residues.

Although any amino acid residue can be present in $X_1$ and $X_2$, reactive side chains such as the mercaptan of cysteine, carboxyl groups such as those of aspartic and glutamic acids, and the ε-amino group of a lysine are typically absent from $X_1$ and $X_2$ sequences, and from Xaa group side chains. Those reactive side chains are also relatively hydrophilic. This absence of hydrophilic side chains is also a function of the active site of this family of enzymes exhibiting a preference for relatively hydrophobic side chains, particularly for the $P_1$ and $P_1'$ positions.

An amino acid residue of $X_1$ and $X_2$ or side chain of Xaa can be present in an oligopeptide analog sequence in either a D- or L-configuration, as is exemplified below wherein all residues are in the L-configuration unless preceded by a "D-". Not only are both D- and L-amino acid residues contemplated for use in an oligopeptide analog, but modified and unusual amino acid residues, amines and carboxylic acids are also contemplated, particularly at or adjacent the amino- and carboxy-termini of an pseudopeptide.

For example, a 2,2-diethylglycine or 2,2-dimethylglycine residue can be present at either or both termini, or a 2-aminoindanol can be amide-bonded to a carboxy-terminal residue to form a 2-amidoindanol group. Similarly, a $C_1$–$C_6$ acyl group as discussed previously such as 3-methylbutanoyl (isovaleryl; Iva) can be useful at the amino-terminus, whereas 3-methylbutylamine reacted at the carboxy-terminus to form a 3-methylbutylamide (isoamylamide; Iaa) can also be useful as can an aminovalaric acid forming an amylamide (Avl).

The above terminal substituent groups and modified amino acid residues serve at least two functions. First, their presence removes ionic charge from the pseudopeptide to help facilitate passage through membranes. Second, they help protect the pseudopeptide from degradation by other proteinase and peptidase enzymes such as trypsin and carboxypeptidase A that are present in vivo and can otherwise cleave a pseudopeptide.

A contemplated pseudopeptide binds to an aspartic proteinase and inhibits the in vitro activity of the enzyme with an inhibitory constant, $K_i$, of about $10^{-6}$ to about $10^{-11}$, and preferably about $10^{-8}$ to about $10^{-11}$, molar (M) in the presence of a usually assayed native substrate. The sequence of a contemplated pseudopeptide is that of an oligopeptide, oligopeptide analog, protein or polyprotein (substrate) that is reversibly bound by a given aspartic proteinase, except for the phosphonamidate ester linkage as is illustrated before.

The $K_i$ value of a contemplated inhibitor can also be viewed relative to the dissociation constant of a usual substrate for the enzyme, as is angiotensinogen for renin. A contemplated inhibitor binds to its aspartic proteinase about $10^5$ to about $10^6$ times more tightly than does the usual substrate. Thus, where the dissociation constant for the enzyme and its substrate is about $10^{-3}$, the dissociation constant for the same enzyme and a contemplated inhibitor is about $10^{-8}$ to about $10^{-9}$.

Although the mechanisms of action of the aspartic proteinase family of enzymes are substantially identical, the enzymes exhibit different binding and cleaving properties with different substrates and inhibitors. Thus, different inhibitor sequences are utilized with different members of the aspartyl proteinase family. Each of the contemplated different sequences nevertheless contains a phosphinate methylene ammonium link between the $P_1$ and $P_1'$ residues of the inhibitor.

Table 1 below lists illustrative members of the aspartic proteinase enzyme family and exemplary, contemplated inhibitors form for each listed enzyme.

TABLE 1

Enzymes and Inhibitors

Cathepsin D

| | |
|---|---|
| t-BOC-D-Phe-Pro-Pheψ[PO(OH)CH$_2$NH]Phe-Val-D-Trp | (SEQ ID No: 1) |
| t-BOC-D-Phe-Pro-Pheψ[PO(OH)CH$_2$NH]Phe-Avl | (SEQ ID NO: 2) |
| Gly-Phe-Leu-Gly-Pheψ[PO(OH)CH$_2$NH]Leu | (SEQ ID NO: 3) |
| Gly-D-Phe-Leu-Gly-Pheψ[PO(OH)CH$_2$NH]Leu | (SEQ ID NO: 4) |
| Gly-Phe-D-Leu-Gly-Pheψ[PO(OH)CH$_2$NH]Leu | (SEQ ID NO: 5) |
| Gly-Phe-Leu-Gly-D-Pheψ[PO(OH)CH$_2$NH]Leu-OC$_2$H$_5$ | (SEQ ID NO: 6) |

Renin

| | |
|---|---|
| His-Pro-Phe-His-Leuψ[PO(OH)CH$_2$NH]Val-Ile-His | (SEQ ID NO: 7) |
| t-BOC-His-Pro-Phe-His-Leuψ[PO(OH)CH$_2$NH]Val-Ile-His | (SEQ ID NO: 8) |
| Pro-His-Pro-Phe-His-Pheψ[PO(OH)CH$_2$NH]Phe-Val-Tyr-Lys | (SEQ ID NO: 9) |
| Arg-Arg-Pro-Phe-His-Leuψ[PO(OH)CH$_2$NH]Val-Ile-His-Lys(t-BOC)-OCH$_3$ | (SEQ ID NO: 10) |
| His-Pro-Phe-His-Leuψ[PO(OH)CH$_2$NH]Leu-Val-Tyr | (SEQ ID NO: 11) |
| His-Pro-Phe-His-Pheψ[PO(OH)CH$_2$NH]Phe-Val-Tyr | (SEQ ID NO: 12) |
| Asp-Arg-Val-Tyr-Ile-His-Pro-Phe-His-Leuψ[PO(OH)CH$_2$NH]Val-Ile-His | (SEQ ID NO: 13) |

Chymosin

| | |
|---|---|
| CH$_3$C(O)-Leu-Ser-Pheψ[PO(OH)CH$_2$NH]Met-Ala-Ile-Pro-Pro-Lys-Lys | (SEQ ID NO: 14) |
| CH$_3$C(O)-Val-Val-Leuψ[PO(OH)CH$_2$NH]Ala-Leu | (SEQ ID NO: 15) |

Penicillopepsin

| | |
|---|---|
| Iva-Val-Val-Leuψ[PO(OH)CH$_2$NH]Phe-OCH$_3$ | (SEQ ID NO: 16) |
| Iva-Val-Val-Leuψ[PO(OH)CH$_2$NH]Phe-Ala-Ala-OCH$_3$ | (SEQ ID NO: 17) |

Pepsin

| | |
|---|---|
| Leu-Val-homoArg-Val-Pro-Leuψ[PO(OH)CH$_2$NH]Val-Arg-homoArg-homoArg-Ser-Leu-Arg-Gln-Leu-Ile | (SEQ ID NO: 18) |
| CH$_3$C(O)-Val-Val-Leuψ[PO(OH)CH$_2$NH]Ala-Ala-Leu | (SEQ ID NO: 19) |
| Val-Val-Leuψ[PO(OH)CH$_2$NH]Ala-Ala-Leu | (SEQ ID NO: 20) |
| Iva-Val-Leuψ[PO(OH)CH$_2$NH]Ala-Ala-Iaa | (SEQ ID NO: 21) |
| Iva-Val-Val-Leuψ[PO(OH)CH$_2$NH]Ala-Ala-OC$_2$H$_5$ | (SEQ ID NO: 22) |

TABLE 1-continued

Enzymes and Inhibitors

HIV-1 Proteinase

| | |
|---|---|
| $CH_3C(O)$-Ser-Leu-Asn-Pheψ[PO(OH)$CH_2$N]Pro-Ile-Val-$OCH_3$ | (SEQ ID NO: 23) |
| $C_5H_{11}C(O)$-Ser-Leu-Asn-Pheψ[PO(OH)$CH_2$N]Pro-Ile-Val-$OCH_3$ | (SEQ ID NO: 24) |
| $CH_3C(O)$-Ser-<u>D</u>-Leu-Asn-Pheψ[PO(OH)$CH_2$N]Pro-Ile-Val-$OCH_3$ | (SEQ ID NO: 25) |
| $CH_3C(O)$-Ser-Leu-Asn-Tyrψ[PO(OH)$CH_2$N]Pro-Ile-Val-$OCH_3$ | (SEQ ID NO: 26) |
| $CH_3C(O)$-Ser-Leu-Asn-Pheψ[PO(OH)$CH_2$N]PIC-NH-$^t$Bu* | (SEQ ID NO: 27) |
| $CH_3C(O)$-Ser-Leu-Asn-Pheψ[PO(OH)$CH_2$N]DIQ-NH-$^t$Bu* | (SEQ ID NO: 28) |
| $CH_3C(O)$-Leu-Asn-Pheψ[PO(OH)$CH_2$N ]PIC-NH-$^t$Bu* | (SEQ ID NO: 29) |
| $CH_3C(O)$-Leu-Asn-Pheψ[PO(OH)$CH_2$N]DIQ-NH-$^t$Bu* | (SEQ ID NO: 30) |
| QC-Asn-Pheψ[PO(OH)$CH_2$N]PIC-NH-$^t$Bu* | |
| QC-Asn-Pheψ[PO(OH)$CH_2$N]DIQ-NH-$^t$Bu* | |

*QC = quinoline-2-carbonyl; PIC = piperidine-2(S)-carbonyl; DIQ = (4aS,8aS)-decahydro-3(S)-isoquinoline carbonyl; and $^t$Bu = tert-butyl.

III. Pseudopeptide Syntheses

Synthesis of a contemplated pseudopeptide is relatively straightforward inasmuch as most of the molecule's length is constituted by oligopeptides. One preferred method utilizes a first preprepared oligopeptide for the $P_2$-containing portion ($X_1$-Xaa) and a second preprepared oligopeptide for the $P_1'$-containing portion ($X_2$). Those two portions are then joined to the phosphorus-containing segment to form the molecule.

An exemplary synthesis for a HIV-1 oligopseudopeptide inhibitor having the sequence $CH_3C(O)$-Ser-Leu-Asn-Pheψ[$PO_2^-CH_2NH^+$]Pro-Ile-Val-$OCH_3$ (SEQ ID NO: 23) is provided below.

Synthesis of the above oligopseudopeptide began with the N-carbobenzoxy (CBZ) phosphinic acid analog, Compound 1. [Baylis et al., *J. Chem. Soc., Perkin Trans. I*, 2845 (1984).] Those authors reported preparation of several amino acid analog phosphonous acids using several related techniques. Illustratively, an aldehyde having the desired amino acid side chain is reacted with the diphenylmethylamine salt of hypophosphorous acid in refluxing dioxane. The diphenylmethyl group could be subsequently cleaved using hydrobromic acid at 100° C. for 45–120 minutes. The desired CBZ derivative can then be prepared using usual techniques. Those authors also reported resolving the CBZ blocked phosphonous acids by salt formation in refluxing ethanol with (+)-α-methylbenzylamine.

Reaction of Compound 1 with trimethylsilyl chloride (TMS-Cl) in methylene chloride in the presence of triethylamine ($ET_3N$) at 5° C. for about four hours followed by reaction with formaldehyde ($CH_2O$) and then reaction with trimethyl phosphite [$P(OMe)_3$] at 90° C. for about five hours produced Compound 2 in about 70 percent yield. Reaction of Compound 2 with trifluoromethanesulfonyl chloride in methylene chloride in the presence of 4-dimethylaminopyridine (DMAP) and $ET_3N$ at about −50° C. for about two hours converted the hydroxymethyl group to a trifluoromethanesulfonate ester, Compound 3. These steps are summarized in Scheme 1, below.

Scheme 1

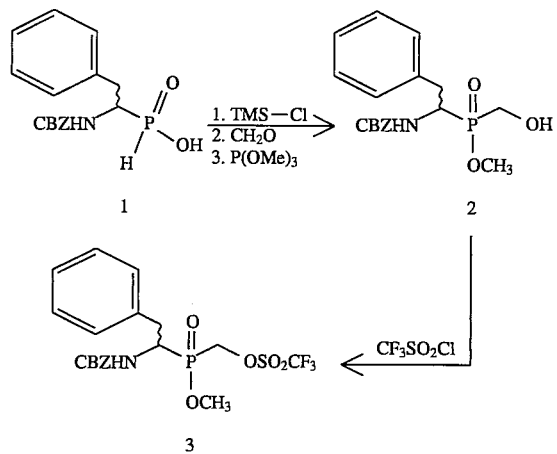

Synthesis of the remainder of the oligopseudopeptide was carried out as outlined in Scheme 2, and discussed below.

Scheme 2

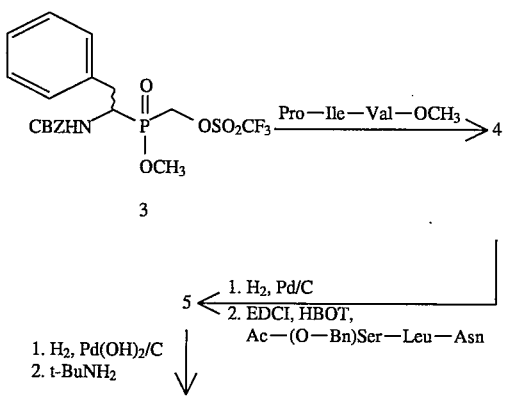

-continued
Scheme 2

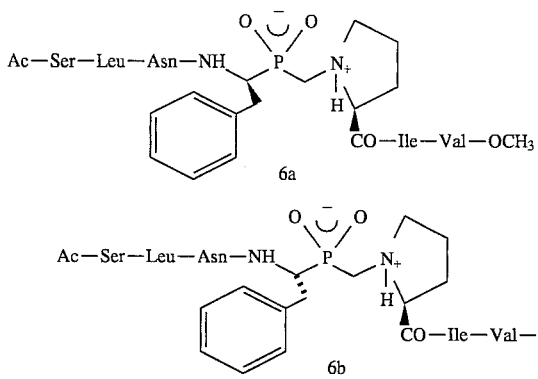

Reaction of Compound 3 with the previously prepared tripeptide methyl ester, Pro-Ile-Val-OCH$_3$, provided a tetrapseudopeptide, Compound 4, containing the surrogate $P_1$-$P_1'$ bond, as well as residues $P_2'$ and $P_3'$. The reaction was carried out in tetrahydrofuran (THF) at room temperature for about three hours to provide Compound 4 in about 65 percent yield.

The CBZ group of Compound 4 was deprotected by hydrogenolysis over palladium on carbon at room temperature using a solvent of methanol/ethyl acetate and a reaction time of about three hours. The previously prepared blocked tripeptide, Ac-(O-benzyl)Ser-Leu-Asn, was coupled to Compound 4 by reaction with ethyl[(dimethylamino)propyl] carbodiimide (EDCI) in an ethyl acetate/DMF mixture as solvent in the presence of 1-hydroxybenzotriazole (HBOT) at 5° C. for about 24 hours to form the blocked heptapseudopeptide, Compound 5, in about 60 percent yield. The O-benzyl (O-Bn) protecting group was thereafter removed by hydrogenolysis over palladium hydroxide on carbon [Pd(OH)$_2$/C] at room temperature in a methanol/acetic acid solvent for about 18 hours. That deprotection step was followed by removal of the phosphinic methyl ester by reaction in dry t-butylamine (t-BuNH$_2$) at about 40°–50° C. to provide the deblocked, heptapseudopeptide, Compound 6, in about 50 percent yield as a mixture of enantiomers, Compounds 6a and 6b, whose specific stereochemistry at the $P_1$ residue is not known and is shown illustratively above.

Separation of enantiomers can be carried out at any of several steps. For example, the blocked phosphonous acid, Compound 1, can be resolved by salt formation using a usual amine resolving agent such as brucine or α-methylbenzylamine. Similarly, the deprotected tetrapseudopeptide formed after removal of the CBZ group from Compound 4 can be resolved by salt formation using R-tartaric acid. Where the carboxy-terminus of a completed oligopseudopeptide inhibitor contains a free carboxylic acid, resolution can again be carried out with brucine. Similarly, where the completed oligopseudopeptide contains a free N-terminal amine group, R-tartaric acid can be used for resoltuion. An oligopseudopeptide ester such as Compound 5 contains a second chiral center at the phosphorus atom due to the presence of the ester group so that Compound 5 exists as a pair of diastereomers that can be separated chromatographically as was done here. Subsequent removal of the ester group from the separated diastereomers removes the phosphorus chiral center and provides enantiomeric Compounds 6a and 6b. Still further methods of resolution well known to skilled workers can also be utilized.

The before-described preprepared oligopeptides that constitute the $X_1$ and $X_2$ portions of an inhibitor pseudopeptide can be prepared by any well known method. The two blocked tripeptides used herein were prepared by standard solution reactions. Solid phase techniques pioneered by Merrifield are also useful. Both solution and solid phase synthetic methods are well known by those skilled in the art.

An $R^1$ group that is a $C_1$–$C_6$ acyl group can be added to the $P_2$-containing peptide portion ($X_1$-Xaa) while that peptide is on its synthesis resin or by addition of an N-acetyl blocked (Ac) amino acid during synthesis as was done here. A trifluoroacetyl or t-BOC group is preferably added after cleavage of the peptide from its synthesis resin.

A Z group is preferably added to its $P_1'$-containing peptide portion ($X_2$) after the peptide is cleaved from the resin when solid phase techniques are used. Well known ester- and amide-forming reactions are used for addition of a Z group, and as such reactions are so well known, they will not be dealt with herein. In the present instance, valine methyl ester hydrochloride was used as a starting material so post coupling esterification was unnecessary.

Syntheses of the shorter pseudopeptides as used to inhibit the HIV-1 virus are similar to those. discussed above, and hereinafter. Thus, for example, the QC group can be added at the stage at which the acetyl group is added to a peptide using the acid halide or anhydride. Similarly, a PIC-NH-tBu or DIQ-NH-Bu group can first be synthesized from their respective amino acids and then reacted with a phosphoruscontaining compound such as Compound 3 as is shown in Scheme 2, above, instead of using the tripeptide ester shown in that scheme.

IV. Pharmaceutical Compositions

A pharmaceutical composition is also contemplated that contains a before-described pseudopeptide of the invention as active agent dissolved or dispersed in a physiologically tolerable carrier or diluent. A pseudopeptide inhibitor is present in such a composition in an amount sufficient to inhibit the aspartic proteinase activity of a chosen aspartic proteinase (an effective inhibitory amount).

A pharmaceutical composition is prepared by any of the methods well known in the art of pharmacy all of which involve bringing into association the pseudopeptide active agent and the carrier therefor. For therapeutic use, a pseudopeptide utilized in the present invention can be administered in the form of conventional pharmaceutical compositions. Such compositions can be formulated so as to be suitable for oral or parenteral administration, or as suppositories. In these compositions, the agent is typically dissolved or dispersed in a physiologically tolerable carrier or diluent.

A carrier or diluent is a material useful for administering the active compound and must be "pharmaceutically acceptable" in the sense of being compatible with the other ingredients of the composition and not deleterious to the recipient thereof. Thus, as used herein, the phrases "physiologically tolerable" or "pharmaceutically acceptable" are used interchangeably and refer to molecular entities and compositions that do not produce an allergic or similar untoward reaction, such as gastric upset, dizziness and the like, when administered to a mammal. The physiologically tolerable carrier can take a wide variety of forms depending upon the preparation desired for administration and the intended route of administration.

As an example of a useful composition, a compound of the invention (active agent) can be utilized, dissolved or dispersed in a liquid composition such as a sterile suspension or solution, or as isotonic preparation containing suitable preservatives. Particularly well-suited for the present purposes are injectable media constituted by aqueous injectable buffered or unbuffered isotonic and sterile saline or glucose solutions, as well as water alone, or an aqueous ethanol solution. Additional liquid forms in which these compounds can be incorporated for administration include flavored emulsions with edible oils such as cottonseed oil, sesame oil, coconut oil, peanut oil, and the like, as well as elixirs and similar pharmaceutical vehicles. Exemplary further liquid diluents can be found in *Remmington's Pharmaceutical Sciences*, Hack Publishing Co., Easton, Pa. (1980).

An active agent can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, pharmaceutically acceptable and metabolizable lipid capable of forming liposomes can be used. The present compositions in liposome form can contain stabilizers, preservatives, excipients, and the like in addition to the agent. The preferred lipids are the phospholipids and the phosphatidyl cholines (lecithins), both natural and synthetic.

Methods of forming liposomes are known in the art. See, for example, Prescott, Ed., *Methods in cell Biology*, Vol. XIV, Academic press, New York, N.Y. (1976), p.33 et seq.

An active agent pseudopeptide can also be used in compositions such as tablets or pills, preferably containing a unit dose of the compound. To this end, the agent (active ingredient) is mixed with conventional tableting ingredients such as corn starch, lactose, sucrose, sorbitol, talc, stearic acid, magnesium stearate, dicalcium phosphate, gums, or similar materials as non-toxic, physiologically tolerable carriers. The tablets or pills can be laminated or otherwise compounded to provide unit dosage forms affording prolonged or delayed action.

It should be understood that in addition to the aforementioned carrier ingredients the pharmaceutical composition described herein can include, as appropriate, one or more additional carrier ingredients such as diluents, buffers, flavoring agents, binders, surface active agents, thickeners, lubricants, preservatives (including antioxidants) and the like, and substances included for the purpose of rendering the formulation isotonic with the blood of the intended recipient.

The tablets or pills can also be provided with an enteric layer in the form of an envelope that serves to resist disintegration in the stomach and permits the active ingredient to pass intact into the duodenum or to be delayed in release. A variety of materials can be used for such enteric layers or coatings, including polymeric acids or mixtures of such acids with such materials as shellac, shellac and cetyl alcohol, cellulose acetate phthalate, and the like. A particularly suitable enteric coating comprises a styrene-maleic acid copolymer together with known materials that contribute to the enteric properties of the coating. Methods for producing enteric coated tablets are described in U.S. Pat. No. 4,079,125 to Sipos, which is herein incorporated by reference.

The term "unit dose", as used herein, refers to physically discrete units suitable as unitary dosages for administration to warm blooded animals, each such unit containing a predetermined quantity of the agent calculated to produce the desired therapeutic effect in association with the pharmaceutically acceptable diluent. Examples of suitable unit dosage forms in accord with this invention are tablets, capsules, pills, powder packets, granules, wafers, cachets, teaspoonfuls, dropperfuls, ampules, vials, segregated multiples of any of the foregoing, and the like.

A pseudopeptide of the invention is present in such a pharmaceutical composition in an amount effective to achieve the desired inhibition. For example, where in vitro enzyme inhibition is the desired result, a compound of the invention can be utilized in an amount sufficient to provide a concentration of about 0.01 to about 2,000 nanomolar (nM) with enzyme concentration of about 1 nM to about 1 µM, and a substrate concentration of about 10 to about 2,000 micromolar (µM). The amounts of enzyme, substrate and inhibitor used are largely a function of convenience, with the substrate typically being in large excess over the enzyme (e.g. 100–10,00 fold excess). For in vivo use, an effective amount of a compound of the invention is about 0.1 to about 50 mg per kilogram of body weight or an-amount sufficient to provide a concentration of about 0.01 to about 100 µg/mL to the bloodstream.

V. Methods

A method of inhibiting an aspartic proteinase is also contemplated. Here, a pharmaceutical composition as discussed before that contains an aspartic proteinase inhibiting amount of a before-discussed pseudopeptide is admixed in an aqueous medium with an aspartic proteinase in the presence of a substrate for the enzyme to form an inhibition mixture. The inhibition mixture is maintained for a time period sufficient for the inhibitor to inhibit the aspartic proteinase, typically five minutes to five hours.

When carried out in vitro, as where the binding properties or mechanism of action of the enzyme is studied, for example, the inhibition reaction is typically followed spectrophotometrically. The aqueous medium in such a case is typically a buffer solution. Exemplary in vitro techniques are disclosed hereinafter.

When the inhibition reaction is carried out in vivo as where renin is the enzyme to be inhibited, the aqueous medium is constituted by a body fluid such as blood, lymph, stomach fluid or the like, and inhibition of the enzyme is assayed by a body function, as by blood pressure lowering for renin. An exemplary assay is discussed hereinafter.

VI. Assay Procedures

Assay procedures for aspartic proteinase enzymes are well known in the art. As a consequence, only a few such assays are described herein as exemplary.

A. In Vitro Pepsin Inhibition Assay

Porcine stomach mucosa pepsin (Sigma Chemical Co.) is chromatographically purified and is dissolved and diluted immediately prior to use in a 0.1M sodium acetate buffer at pH 3.5. A useful substrate is the octapeptide analog:

Lys-pro-Ala-Glu-phe-p($NO_2$)Phe-Arg-Leu (SEQ ID NO:31) as discussed in Bartlett et al., *J. Org. Chem.*, 55:6268 (1990). Initial rates of substrate hydrolysis are determined by equilibrating substrate and pseudopeptide inhibitor solutions at 37° C. in a cuvette for about three minutes, followed by initiation of the reaction by addition of 3.0 pmoles of pepsin per 1.00 mL final volume. Substrate hydrolysis is measured by observing the decrease in absorbance at 310 nm. Initial rates are measured from 0.5 minutes until no more than 10 percent of the substrate is hydrolyzed. Inhibition constants are then determined by usual means.

B. In Vitro Renin Inhibition Assay

Purified human renin [Stein et al., *J. Fed. Proc,, Fed. Am. Soc. Exp. Biol.*, 44:1363 (1985)] is assayed using pure angiotensinogen [Dorer et al., *Anal. Biochem.*, 87:11 (1978)] at pH 6.0 in maleate buffer. Inhibitors are dissolved in DMSO and diluted so that prior to addition of the assay system, the solutions contain 10 percent DMSO and 0.5 percent bovine serum albumin (BSA). The final incubation mixture (100 µL) contains 0.135M maleate buffer at pH 6.0, EDTA at 3 mM, phenylmethanesulfonyl fluoride at 1.4 mM, 0.21 µM angiotensinogen, 0.24 mGU [Bangham et al., *Clin,*

*Sci. Mole. Med.*, 48:1355 (1975)], BSA 0.44 percent and DMSO at 1 percent.

Several concentrations of inhibitor pseudopeptide that bracket the $IC_{50}$ value (the concentration that inhibits 50 percent activity) are preincubated with renin for about five minutes at 37° C. The substrate is then added and incubation is continued for about 10 minutes. The reaction is stopped by freezing the solution in a methanol/dry ice bath, and after thawing at 4° C., an aliquot is analyzed for angiotensin I by use of a commercial kit (NEN Research). The percent inhibition of the hydrolysis reaction is determined and an $IC_{50}$ value is calculated by regression analysis.

C. In Vivo Renin Inhibition Assay

The hypotensive activity of an inhibitor pseudopeptide in anesthetized, sodium depleted marmosets is used in this assay. The fall in mean arterial pressure (MAP) over a two-hour time period is used as the assayed value.

An internal standard using a known hypotensive drug such as captopril (at 1.0 mg/kg, iv) or the compound designated CGP 385-60A [Buhlmayer et al., *J. Med. Chem.*, 31:1839 (1988); DeGasparo et al., *J. Clin. Pharmac.*, 27:587 (1989)] as used in this model can also be used.

For intravenous (iv) dosage, inhibitor is provided in a pharmaceutical composition at about 1–5 mg/kg. For peroral (po) administration, amounts on the order of 10–100 mg/kg are utilized.

The marmosets used for the study are depleted of sodium for two days by treatment with furosemide at 25 mg/kg/day po and a low sodium diet. A final dose of furosemide is administered one hour prior to anesthesia with Inactin at 120 mg/kg intraperitoneally (ip) followed by a 10 mg/kg/hour iv maintenance infusion.

Blood pressure is measured from a catheter in the carotid artery via a Gould Stratham P23 pressure transducer and Lectromed M19 chart recorder. The jugular vein is cannulated for inhibitor injection and anesthetic infusion. Each animal serves as it own blood pressure control D. Procedure for HPLC Assay of HIV-1 PR Inhibition Typical reactions were carried out at room temperature (25° C.) in 150 µl total volumes of 100 mM MES buffer, pH 6.2, containing 1 mM ethylenediaminetetra-acetic acid (EDTA) and 2 mM dithiothreitol (DTT) plus 0.1 percent (v/v) Triton X-100.

Synthetic HIV-1 proteinase [0.5 µg, obtained from Dr. Stephen Kent of The Scripps Research Institute; see *Cell*, 54:363–368 (July 29, 1988)] was first incubated in buffer with (or without) various concentrations of "inhibitor(s)" for 30 minutes at 25° C. The proteinase reaction was then initiated by the addition of HIV substrate IV (Bachem Bioscience Inc.) at fixed concentrations. HIV Substrate IV has the sequence Lys-Ala-Arg-Val-Nle-p-NO$_2$Phe-Glu-Ala-Nle-NH$_2$ (SEQ ID NO: 32).

At three appropriate times (normally 15, 30 and 45 minutes) the hydrolysis was stopped by adding a 40 µl aliquot from the reaction to 40 µl of a prepared quench solution. The quench solution was 1:4 acetonitrile:water (3 percent trifluoroacetic acid; TFA) and contained 150 µM m-toluic acid which served as an HPLC standard. Quenched aliquots were injected into a reversed-phase HPLC (Hitachi instrument; VYDAC $C_{18}$ column No. 201TP54) and eluted with an isocratic mixture of 20 percent acetonitrile/80 percent water (0.1 percent TFA) flowing at 2.0 m./min. Reaction progress was monitored by following the increasing absorbance (peak height) of the substrate IV cleavage product detected at 254 nM.

Inhibition studies indicated that one stereoisomer of Compound 6 had a $K_i$ of about 600 µM, whereas the other isomer $K_i$ value was about 10±5 nM. The results for the more active isomer compare favorably with the $K_i$ results obtained by Rich et al., *J. Med. Chem.*, 33:1288 (1990) of 0.66 nM for a pseudopeptide having the same sequence as Compound 6, but whose $P_1$-$P_1'$ bond included a —CHOHCH$_2$— group linked to the proline nitrogen to form a hydroxyethylamine isostere. Krohn et al., *J. Med. Chem.*, 34:3340 (1991) reported $IC_{50}$ values of 0.6 and 0.24 nM for the R,S- and S-forms, respectively, of that same pseudopeptide.

The above, present, results also compare favorably with the results of Roberts et al., *Science*, 248:358 (1991) who also used the hydroxyethylamine isostere and reported $IC_{50}$ values of several hundred to less than 0.4 nanomolar for compounds such as CBZ -Asn-Pheψ[CH(OH)CH$_2$N]Pro-O$^t$Bu;

QC-Asn-Pheψ[CH(OH)CH$_2$N]PIC-NH-$^t$Bu; and

QC-Asn-Pheψ[CH(OH)CH$_2$N]DIQ-NH-$^t$Bu, where CBZ, $^t$Bu QC PIC and DIQ are as previously defined. Those authors also reported differences in $IC_{50}$ values of about 2- to about 20-fold based upon the R or S stereochemistry of the hydroxyethylamine isostere, with the R isomers having greater activity. The peptide bond surrogate of the present invention is achiral and therefore does not present the R,S-isomeric problems of a hydroxyethylamine isostere.

VII. Oligopeptide Syntheses

The two tripeptides illustrated in Scheme 2 were prepared using solution reactions as discussed below.

A. Preparation of Pro-Ile-Val-OCH$_3$

BOC-isoleucine was coupled to valine methyl ester hydrochloride using EDCI in the presence of N-methyl morpholine and HOBT in DMF/ethyl acetate at room temperature to form the N-blocked dipeptide methyl in about 95 percent yield. The BOC group was removed with TFA in methylene chloride at room temperature for about one hour, and the resulting dipeptide methyl ester was neutralized with sodium bicarbonate to provide the deprotected dipeptide methyl ester in about 98 percent yield.

The deprotected dipeptide methyl ester was then coupled to CBZ-proline as above using a reaction time of about four hours to provide the N-blocked tripeptdie methyl ester in about 90 percent yield. Hydrogenolysis using Pd/C at room temperature for about three hours provided the title compound in about 90 percent yield. The overall yield was thus about 75 percent.

B. Preparation of Ac-(O-Bn)Ser-Leu-Asn

BOC-(O-Bn)serine was coupled with leucine methyl ester hydrochloride as described before using a three-hour reaction time to provide the doubly blocked dipeptide methyl ester in about 95 percent yield. The BOC group was removed as discussed before and the resulting N-terminal amine was acetylated using acetic anhydride in pyridine at room temperature for three hours to provide the blocked dipeptide methyl ester, (N-acetyl) Ac-(O-Bn)Ser-Leu-OCH$_3$, in about 96 percent yield. The methyl ester was removed by reaction with 1N sodium hydroxide in THF at room temperature for about three hours to provide the blocked dipeptide free acid in about 90 percent yield.

The blocked dipeptide free acid was coupled with asparigine t-butyl ester hydrochloride as described before to provide the blocked tripeptide t-butyl ester in about 90 percent yield. The t-butyl ester was removed by reaction with TFA in methylene chloride at room temperature for about one hour to provide the title compound in about 90 percent yield. The overall yield here was about 66 percent.

Although the present invention has now been described in terms of certain preferred embodiments, and exemplified with respect thereto, one skilled in the art will readily appreciate that various modifications, changes, omissions and substitutions may be made without departing from the spirit thereof.

We claim:

1. A linkage unit for joining two peptide sequences, i.e. an amino terminal peptide sequence and a carboxyl terminal peptide sequence, the linkage unit comprising:

a dipeptide modified as set out below and having a first amino acid residue ($aa_1$), a second amino acid residue ($aa_2$), and an exploded linkage between said first and second amino acid residues, said modified dipeptide being represented by the formula:

($aa_1$—POOH)—$CH_2$—(NR—$aa_2$) at acid pH said first amino acid residue lacking a backbone carbonyl group and having, instead, a phosphinic acid group, i.e. ($aa_1$—POOH—), said first amino acid residue being an α-amino acid residue and having an amino acid side chain other than H, said second amino acid residue having a backbone amino group, i.e. (—NR—$aa_2$), where R is H if the backbone amine group of said second amino acid is a primary amine or R is a carbon atom forming part of the said second amino acid residue ($aa_2$) if the backbone amine group of said second amino acid is a secondary amine, said exploded linkage between said first and second amino acid residues lacking a peptide bond and having, instead, a methylene group, said methylene group having a first bond connecting said methylene group to said phosphinic acid group of said first amino acid residue, said methylene group having a second bond connecting said methylene group to the backbone amino group of said second amino acid residue, whereby said first amino acid residue ($aa_1$) of said dipeptide being employable for forming a peptide linkage with said amino terminal peptide sequence and said second amino acid residue ($aa_2$) of said dipeptide being employable for forming a peptide linkage with said carboxyl terminal peptide sequence, thereby linking said amino terminal peptide sequence to said carboxyl terminal peptide sequence with said exploded linkage containing said methylene group.

2. A linkage unit as described in claim 1 wherein:

the phosphinic acid methylene amino bonds of said exploded linkage being converted, near physiological pH, to zwitterionic phosphinate methylene ammonium bonds represented within said dipeptide by the formula:

($aa_1$—POO—)—$CH_2$—($NHR^+$—$aa_2$)

3. A modified dipeptide employable as a peptide linkage unit, the modified dipeptide being represented at acid pH by the formula:

($aa_1$—POOH)—($CH_2$)—(NR—$aa_2$)

where ($aa_1$—POOH) represents a first amino acid residue and (NR—$aa_2$) represents a second amino acid residue, and ($CH_2$) represents an exploded linkage between said first and second amino acid residues, said first amino acid residue being an α-amino acid residue and having an amino acid side chain other than H, said first amino acid residue ($aa_1$—POOH)—lacking a backbone carbonyl group and having in its place a backbone phosphinic acid group, i.e. —POOH—, said second amino acid residue having a backbone amino group, i.e. —NR—, where R is H if the backbone amine group of said second amino acid is a primary amine or R is a carbon atom forming part of the said second amino acid residue ($aa_2$) if the backbone amine group of said second amino acid is a secondary amine, said exploded linkage between said first and said second amino acid residues lacking a peptide bond and having, instead, a methylene group, i.e. —($CH_2$)— said methylene group having a first bond connecting said methylene group to said phospinic acid group of said first amino acid residue, said methylene group having a second bond connecting said methylene group to the backbone amino group of said second amino acid residue.

4. A dipeptide as described in claim 3 wherein:

the phosphinic acid methylene amino bonds of said exploded linkage being converted, near physiological pH, to switterionic phosphinate methylene ammonium bonds represented within said dipeptide by the formula ($aa_1$—$POO^-$)—$CH_2$—($NHR^+$—$aa_2$).

5. An improved polypeptide having an amino terminal peptide sequence, a carboxyl terminal peptide sequence, and a linkage unit for joining said amino terminal peptide and said carboxyl terminal peptide, wherein the improvement comprises:

said linkage unit including a dipeptide having a first amino acid residue ($aa_1$), a second amino acid residue ($aa_2$), and an exploded linkage between said first and second amino acid residues, said first amino acid residue being the residue of an α-amino acid but lacking a backbone carbonyl group and having, instead, a phosphinic acid group, i.e. ($aa_1$—POOH—), said second amino acid residue having a backbone amino group i.e. (—NR—$aa_2$), where R is H if the backbone amine group of said second amino acid is a primary amine or R is a carbon atom forming part of the said second amino acid residue ($aa_2$) if the backbone amine group of said second amino acid is a secondary amine, said exploded linkage between said first and said second amino acid residues lacking a peptide bond and having, instead, a methylene group, said methylene group having a first bond connecting said methylene group to said phosphinic acid group of said first amino acid residue, said methylene group having a second bond connecting said methylene group to the backbone amino group of said second amino acid residue, said dipeptide and said exploded linkage being represented by the formula:

($aa_1$—POOH)—$CH_2$—(NR—$aa_2$) at acid pH, said first amino acid residue ($aa_1$) of said dipeptide having a peptide linkage with said amino terminal peptide sequence, said second amino acid residue ($aa_2$) of said dipeptide having a peptide linkage with said carboxyl terminal peptide sequence, wherein said amino terminal peptide sequence is linked to said carboxy terminal peptide sequence by means of said dipeptide.

6. An improved polypeptide as described in claim 5, wherein the improvement further comprises:

the phosphinic acid methylene amino bonds of said exploded linkage being converted, near physiological pH, to switterionic phosphinate methylene ammonium bonds represented within said dipeptide by the formula:

($aa_1$—$POO^-$)—$CH_2$—($NHR^+$—$aa_2$).

7. A peptide comprising:

a linkage unit having a dipeptide with a first amino acid residue ($aa_1$), a second amino acid residue ($aa_2$), and an exploded linkage between said first and second amino acid residues, and a third amino acid linked by means of a backbone peptide bond to said linkage unit, said first amino acid residue being an α-amino acid residue but lacking a backbone carbonyl group and having, instead, a phosphinic acid group, i.e. ($aa_1$—POOH—), said second amino acid residue having a backbone amino group, i.e. (—NR—$aa_2$), where R is H if the backbone amine group of said second amino acid is a primary amine or R is a carbon atom forming part of the said second amino acid residue ($aa_2$) if the backbone amine group of said second amino acid is a secondary amine, said exploded linkage between said first and second amino acid residues lacking a peptide bond and having, instead, a methylene group, said methylene group having a first bond connecting said methylene group to said phosphinic acid group of said first amino acid residue, said methylene group having a second bond connecting said methylene group to the backbone amino group of said second amino acid residue, said dipeptide and said exploded linkage being represented at acid pH by the formula:

($aa_1$—POOH)—$CH_2$—(NR—$aa_2$).

8. A method for linking a linkage unit with a flanking amino acid residue, the flanking amino acid having a bondable amino and, the linkage unit being represented at acid pH by the formula ($aa_1$—POOH)—$CH_2$—(NR—$aa_2$), where ($aa_1$—POOH) represents a first amino acid residue and (NR-$aa_1$) represents a second amino acid residue, and ($CH_2$) represents an exploded linkage between said first and second amino acid residues, said first amino acid residue ($aa_1$—POOH)—lacking a backbone carbonyl group and having in its place a backbone phosphinic acid group, i.e. —POOH—, said second amino acid residue having a bondable carboxyl and and a backbone amino group, i.e. —NR—, where R is H if the backbone amino group of said second amino acid is a primary amine or R is a carbon atom forming part of the said second amino acid residue ($aa_2$) if the backbone amino group of said second amino acid is a secondary amine, said exploded linkage between said first and said second amino acid residues lacking a peptide bond and having, instead, a methylene group, i.e. —($CH_2$)— said methylene group having a first bond connecting said methylene group to said phosphinic acid group of said first amino acid residue, said methylene group having a second bond connecting said methylene group to the backbone amino group of said second amino acid residue, the method comprising the following step:

Step A: linking the bondable amino end of the flanking amino acid residue to the bondable carboxyl end of the second amino acid residue of the linkage unit.

9. A method for linking a linkage unit with a flanking amino acid residue, the flanking amino acid having a bondable carboxyl and, the linkage unit being represented at acid pH by the formula (aa$_1$—POOH)—CH$_2$—(NR—aa$_2$), where (aa$_1$—POOH) represents a first amino acid residue and (NR—aa$_2$) represents a second amino acid residue, and (CH$_2$) represents an exploded linkage between said first and second amino acid residues, said first amino acid residue (aa$_1$—POOH)—having a bondable amino end but lacking a backbone carbonyl group, and having in its place a backbone phosphinic acid group, i.e. —POOH—, said second amino acid residue having a backbone amino group, i.e. —NR—, where R is H if the backbone amino group of said second amino acid is a primary amine or R is a carbon atom forming part of the said second amino acid residue (aa$_2$) if the backbone amino group of said second amino acid is a secondary amine, said exploded linkage between said first and said second amino acid residues lacking a peptide bond and having, instead, a methylene group, i.e.—(CH$_2$)— said methylene group having a first bond connecting said methylene group to said phosphinic acid group of said first amino acid residue, said methylene group having a second bond connecting said methylene group to the backbone amino group of said second amino acid residue, the method comprising the following step:

Step A: linking the bondable carboxyl end of the flanking amino acid residue to the bondable amino end of the first amino acid residue of the linkage unit.

10. An aspartic proteinase inhibitor pseudopeptide having a length of 3 to about 15 amino acid residues and containing a $P_1$ to $P_1'$ bond constituted by a phosphinic and methylene amine linkage in which the phosphorus atom is bonded (i) to $P_1$ in place of the carbonyl carbon atom of a peptide bond and (ii) to a methylene amino group in place of the amide nitrogen atom of a peptide bond.

11. The inhibitor of claim 10 wherein said pseudopeptide is a carboxy-terminal $C_1$-$C_6$ alkyl ester.

12. The inhibitor of claim 10 wherein said inhibitor has a length of 4 to about 10 amino acid residues.

13. A pseudopeptide aspartic proteinase inhibitor of the formula

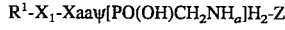

wherein $X_1$ is an amino acid residue or oligopeptide containing a sequence of up to about ten amino acid residues;

a is zero, one or two;

Xaa is a surrogate amino acid residue having an amino acid side chain;

$X_2$ is an amino acid residue or oligopeptide containing a sequence of up to about ten amino acid residues;

Z is selected from the group consisting of NH$_2$, NH—C$_1$-C$_6$ acyl, OH, O—C$_1$-C$_6$ alkyl and 2-amido-indanol; and R$^1$ is selected from the group consisting of hydrogen, C$_1$-C$_6$ acyl, trifluoroacetyl, quinolin-2-ylcarbonyl and t-BOC;

said oligopeptide analog having the length of 3 to about 15 amino acid residues.

14. The pseudopeptide of claim 13 wherein Xaa is a surrogate amino acid having an amino acid side chain selected from the group consisting of Leu, Tyr and Phe, and the amino-terminal residue of $X_2$ is selected from the group consisting of Tyr, Leu, Val, Met, Pro, Ala and Phe.

15. The pseudopeptide of claim 14 whose carboxy-terminal residue is esterified as a $C_1$-$C_6$ alkyl ester.

16. An oligopseudopeptide aspartic proteinase inhibitor of the formula

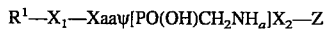

wherein $X_1$ is an amino acid residue or oligopeptide containing a sequence of up to about ten amino acid residues;

a is zero, one or two;

Xaa is an amino acid surrogate having a side chain selected from the group consisting of Leu, Tyr, Val and Phe;

$X_2$ is an amino acid residue or oligopeptide containing a sequence of up to about ten amino acid residues whose amino-terminal residue is selected from the group consisting of Tyr, Leu, Val, Met, Pro, Ala and Phe;

Z is selected from the group consisting of NH$_2$, NH—C$_1$-C$_6$ acyl, OH, O—C$_1$-C$_6$ alkyl and 2-amido-indanol; and R$^1$ is selected from the group consisting of hydrogen, C$_1$-C$_6$ acyl, trifluoroacetyl, quinolin-2-ylcarbonyl and t-BOC said oligopeptide analog having the length of 4 to about 10 amino acid residues.

17. The oligopseudopeptide of claim 16 wherein said aspartyl proteinase is cathepsin D and said oligopseudopeptide has the sequence

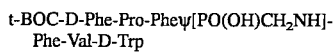
(SEQ ID NO: 1).

18. The oligopseudopeptide of claim 16 wherein said aspartyl proteinase is cathepsin D and said oligopseudopeptide has the sequence

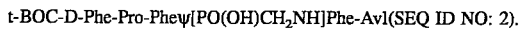(SEQ ID NO: 2).

19. The oligopseudopeptide of claim 16 wherein said aspartyl proteinase is renin and said oligopseudopeptide has the sequence

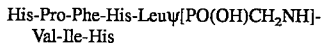
(SEQ ID NO: 7).

20. The oligopseudopeptide of claim 16 wherein said aspartyl proteinase is renin and said oligopseudopeptide has the sequence

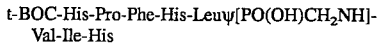
(SEQ ID NO: 8).

21. The oligopseudopeptide of claim 16 wherein said aspartyl proteinase is renin and said oligopseudopeptide has the sequence

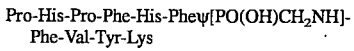
(SEQ ID NO: 9).

22. The oligopseudopeptide of claim 16 wherein said aspartyl proteinase is renin and said oligopseudopeptide has the sequence Arg-Arg-Pro-Phe-His-Leuψ[PO(OH)CH$_2$NH]Val-Ile-His-Lys(t-BOC)-OCH$_3$ (SEQ ID NO:10).

23. The oligopseudopeptide of claim 16 wherein said aspartyl proteinase is renin and said oligopseudopeptide has the sequence His-Pro-Phe-His-Leuψ[PO(OH)CH$_2$NH]-Leu-Val-Tyr (SEQ ID NO: 11).

24. The oligopseudopeptide of claim 16 wherein said aspartyl proteinase is renin and said oligopseudopeptide has the sequence His-Pro-Phe-His-Pheψ[PO(OH)CH$_2$NH]-Phe-Val-Tyr (SEQ ID NO: 12).

25. The oligopseudopeptide of claim 16 wherein said aspartyl proteinase is chymosin and said oligopseudopeptide has the sequence CH$_3$C(O)-Leu-Ser-Pheψ[PO(OH)CH$_2$NH]Met-Ala-Ile-Pro-Pro-Lys-Lys (SEQ ID NO: 14).

26. The oligopseudopeptide of claim 16 wherein said aspartyl proteinase is chymosin and said oligopseudopeptide has the sequence CH$_3$C(O)-Val-Val-Leuψ[PO(OH)CH$_2$NH]-Ala-Leu (SEQ ID NO: 15).

27. The oligopseudopeptide of claim 16 wherein said aspartyl proteinase is penicillopepsin and said oligopseudopeptide has the sequence Iva-Val-Val-Leuψ[PO(OH)CH$_2$NH]Phe-OCH$_3$ (SEQ ID NO: 16).

28. The oligopseudopeptide of claim 16 wherein said aspartyl proteinase is penicillopepsin and said oligopseudopeptide has the sequence Iva-Val-Val-Leuψ[PO(OH)CH$_2$NH]-Phe-Ala-Ala-OCH$_3$ (SEQ ID NO: 17).

29. The oligopseudopeptide of claim 16 wherein said aspartyl proteinase is pepsin and said oligopseudopeptide has the sequence Val-Val-Leuψ[PO(OH)CH$_2$NH]Ala-Ala-Leu (SEQ ID NO: 20).

30. The oligopseudopeptide of claim 16 wherein said aspartyl proteinase is pepsin and said oligopseudopeptide has the sequence Iva-Val-Leuψ[PO(OH)CH$_2$NH]Ala-Ala-Iaa (SEQ ID NO: 21).

31. The oligopseudopeptide of claim 16 wherein said aspartyl proteinase is that of HIV-1 and said oligopseudopeptide has the sequence CH$_3$C(O)-Ser-Leu-Asn-Pheψ[PO(OH)CH$_2$N]-Pro-Ile-Val-OCH$_3$ (SEQ ID NO: 23)

32. The oligopseudopeptide of claim 16 wherein said aspartyl proteinase is that of HIV-1 and said oligopseudopeptide has the sequence C$_5$H$_{11}$C(O)-Ser-Leu-Asn-Pheψ[PO(OH)CH$_2$N]-Pro-Ile-Val-OCH$_3$ (SEQ ID NO: 24)

33. The oligopseudopeptide of claim 16 wherein said aspartyl proteinase is that of HIV-1 and said oligopseudopeptide has the sequence CH$_3$C(O)-Ser-D-Leu-Asn-Pheψ[PO(OH)CH$_2$N]-Pro-Ile-Val-OCH$_3$ (SEQ ID NO: 25).

34. The oligopseudopeptide of claim 16 wherein said aspartyl proteinase is that of HIV-1 and said oligopseudopeptide has the sequence CH$_3$C(O)-Ser-Leu-Asn-Tyrψ[PO(OH)CH$_2$N]-Pro-Ile-Val-OCH$_3$ (SEQ ID NO: 26).

35. The oligopseudopeptide of claim 16 wherein said aspartyl proteinase is that of HIV-1 and said oligopseudopeptide has the sequence CH$_3$C(O)-Ser-Leu-Asn-Pheψ[PO(OH)CH$_2$N]-PIC-NH-$^t$Bu (SEQ ID NO: 27)

wherein PIC-NH-$^t$Bu is piperidine-2(S)-carbonyl tertiary-butyl amide.

36. The oligopseudopeptide of claim 16 wherein said aspartyl proteinase is that of HIV-1 and said oligopseudopeptide has the sequence CH$_3$C(O)-Ser-Leu-Asn-Pheψ[PO(OH)CH$_2$N]-DIQ-NH-$^t$Bu (SEQ ID NO: 28)

wherein DIQ-NH-$^t$Bu is (4aS,8aS)-decahydro-3(S)-isoquinolinecarbonyl tertiary-butylamide.

37. The oligopseudopeptide of claim 16 wherein said aspartyl proteinase is that of HIV-1 and said oligopseudopeptide has the sequence CH$_3$C(O)-Leu-Asn-Pheψ[PO(OH)CH$_2$N]-PIC-NH-$^t$Bu (SEQ ID NO: 29)

wherein PIC-NH-$^t$Bu is piperidine-2(S)-carbonyl tertiary-butyl amide.

38. The oligopseudopeptide of claim 16 wherein said aspartyl proteinase is that of HIV-1 and said oligopseudopeptide has the sequence CH$_3$C(O)-Leu-Asn-Pheψ[PO(OH)CH$_2$N]-DIQ-NH-$^t$Bu (SEQ ID NO: 30)

wherein DIQ-NH-$^t$Bu is (4aS,8aS)-decahydro-3(S)-isoquinolinecarbonyl tertiary-butylamide.

39. The oligopseudopeptide of claim 16 wherein said aspartyl proteinase is that of HIV-1 and said oligopseudopeptide has the sequence QC-Asn-Pheψ[PO(OH)CH$_2$N]PIC-NH-$^t$Bu, wherein PIC-NH-$^t$Bu is piperidine-2(S)-carbonyl tertiary-butyl amide and QC is quinoline-2-carbonyl.

40. The oligopseudopeptide of claim 16 wherein said aspartyl proteinase is that of HIV-1 and said oligopseudopeptide has the sequence QC-Asn-Pheψ[PO(OH)CH$_2$N]DIQ-NH-$^t$Bu, wherein DIQ-NH-$^t$Bu is (4aS,8aS)-decahydro-3(S)-isoquinolinecarbonyl tertiary-butylamide and AC is quinoline-2-carbonyl.

41. A pharmaceutical composition comprising an aspartic proteinase inhibitor pseudopeptide present in an effective inhibitory amount dissolved or dispersed in a physiologically tolerable diluent, said pseudopeptide inhibitor having a length of 3 to about 15 amino acid residues and containing a $P_1$ to $P_1'$ bond that is constituted by a phosphinic acid amine linkage in which the phosphorus atom is bonded (i) to $P_1$ in place of the carbonyl carbon atom of a peptide bond and (ii) to a methylene amine group in place of the amido nitrogen atom of a peptide bond.

42. The pharmaceutical composition of claim 41 wherein said pseudopeptide is esterified as a carboxy-terminal $C_1$–$C_6$ alkyl ester.

43. A method of inhibiting the activity of an aspartic proteinase that comprises admixing in an aqueous medium an aspartic proteinase, a substrate for that enzyme and a pharmaceutical composition containing an effective inhibitory amount of a pseudopeptide inhibitor for that aspartic proteinase to form an inhibitory mixture, said pseudopeptide inhibitor having a length of 3 to about 15 amino acid residues and containing a $P_1$ to $P_1'$ bond that is constituted by a phosphinic acid methylene amine linkage in which the phosphorus atom is bonded (i) to $P_1$ in place of the carbonyl carbon atom of a peptide bond and (ii) a methylene amine group in place of the amido nitrogen atom of a peptide bond; and maintaining said inhibitory mixture for a time period sufficient for said pseudopeptide inhibitor to inhibit the activity of said aspartic proteinase.

44. The method of claim 43 wherein said pseudopeptide is esterified as a carboxy-terminal $C_1$–$C_6$ alkyl ester.

* * * * *

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
       ( A ) LENGTH: 6 amino acids
       ( B ) TYPE: amino acid
       ( C ) STRANDEDNESS: single
       ( D ) TOPOLOGY: linear ( i i ) MOLECULE TYPE: peptide ( i x ) FEATURE:
       ( A ) NAME/KEY: Modified-site
       ( B ) LOCATION: 1
       ( D ) OTHER INFORMATION: /label=Xaa
               / note="Xaa is N-t-BOC-D-Phe"

( i x ) FEATURE:
       ( A ) NAME/KEY: Modified-site
       ( B ) LOCATION: 3
       ( D ) OTHER INFORMATION: /label=Xaa
               / note="Xaa is a Phe whose carbonyl
               group is replaced by PO(OH)CH2 group."

( i x ) FEATURE:
       ( A ) NAME/KEY: Modified-site
       ( B ) LOCATION: 6
       ( D ) OTHER INFORMATION: /label=Xaa
               / note="Xaa is D-Trp"

( x i ) SEQUENCE DESCRIPTION: SEQ ID NO:1:

Xaa   Pro   Xaa   Phe   Val   Xaa
       1                       5

( 2 ) INFORMATION FOR SEQ ID NO:2:

( i ) SEQUENCE CHARACTERISTICS:
       ( A ) LENGTH: 4 amino acids
       ( B ) TYPE: amino acid
       ( C ) STRANDEDNESS: single
       ( D ) TOPOLOGY: linear ( i i ) MOLECULE TYPE: peptide ( i x ) FEATURE:
       ( A ) NAME/KEY: Modified-site
       ( B ) LOCATION: 1
       ( D ) OTHER INFORMATION: /label=Xaa
               / note="Xaa is N-t-BOC-D-Phe"

( i x ) FEATURE:
       ( A ) NAME/KEY: Modified-site
       ( B ) LOCATION: 3
       ( D ) OTHER INFORMATION: /label=Xaa
               / note="Xaa is Phe whose carbonyl
               group is replaced by PO(OH)CH2"

( i x ) FEATURE:
       ( A ) NAME/KEY: Modified-site
       ( B ) LOCATION: 4
       ( D ) OTHER INFORMATION: /label=Xaa
               / note="Xaa is Phe amide bonded to
               aminovaleric acid"

( x i ) SEQUENCE DESCRIPTION: SEQ ID NO:2:

Xaa Pro Xaa Xaa
1

( 2 ) INFORMATION FOR SEQ ID NO:3:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 5
( D ) OTHER INFORMATION: /label=Xaa
/ note="Xaa is Phe whose carbonyl
group is replaced by PO(OH)CH2"

( x i ) SEQUENCE DESCRIPTION: SEQ ID NO:3:

Gly Phe Leu Gly Xaa Leu
1                   5

( 2 ) INFORMATION FOR SEQ ID NO:4:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 2
( D ) OTHER INFORMATION: /label=Xaa
/ note="Xaa is D-Phe"

( i x ) FEATURE:
( A ) NAME/KEY: Modified-site
( B ) LOCATION: 5
( D ) OTHER INFORMATION: /label=Xaa
/ note="Xaa is Phe whose carbonyl
group is replaced by PO(OH)CH2"

( x i ) SEQUENCE DESCRIPTION: SEQ ID NO:4:

Gly Xaa Leu Gly Xaa Leu
1                   5

( 2 ) INFORMATION FOR SEQ ID NO:5:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 3
( D ) OTHER INFORMATION: /label=Xaa
/ note="Xaa is D-Leu"

( i x ) FEATURE:
( A ) NAME/KEY: Modified-site
( B ) LOCATION: 5
( D ) OTHER INFORMATION: /label=Xaa
/ note="Xaa is Phe whose carbonyl
group is replaced by PO(OH)CH2"

( x i ) SEQUENCE DESCRIPTION: SEQ ID NO:5:

Gly Phe Xaa Gly Xaa Leu
 1               5

( 2 ) INFORMATION FOR SEQ ID NO:6:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 5
( D ) OTHER INFORMATION: /label=Xaa
/ note="Xaa is D-Phe whose carbonyl
group is replaced by PO(OH)CH2"

( i x ) FEATURE:
( A ) NAME/KEY: Modified-site
( B ) LOCATION: 6
( D ) OTHER INFORMATION: /label=Xaa
/ note="Xaa is Leu ethyl ester"

( x i ) SEQUENCE DESCRIPTION: SEQ ID NO:6:

Gly Phe Leu Gly Xaa Xaa
 1               5

( 2 ) INFORMATION FOR SEQ ID NO:7:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 5
( D ) OTHER INFORMATION: /label=Xaa
/ note="Xaa is Leu whose carbonyl
group is replaced by PO(OH)CH2"

( x i ) SEQUENCE DESCRIPTION: SEQ ID NO:7:

His Pro Phe His Xaa Val Ile His
 1               5

( 2 ) INFORMATION FOR SEQ ID NO:8:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /label=Xaa
/ note="Xaa is N-t-BOC-His"

( i x ) FEATURE:
( A ) NAME/KEY: Modified-site
( B ) LOCATION: 5
( D ) OTHER INFORMATION: /label=Xaa
/ note="Xaa is Leu whose carbonyl group is replaced by PO(OH)CH2"

( x i ) SEQUENCE DESCRIPTION: SEQ ID NO:8:

Xaa Pro Phe His Xaa Val Ile His
    1            5

( 2 ) INFORMATION FOR SEQ ID NO:9:

( i ) SEQUENCE CHARACTERISTICS:
   ( A ) LENGTH: 10 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Modified-site
   ( B ) LOCATION: 6
   ( D ) OTHER INFORMATION: /label=Xaa
     / note="Xaa is Phe whose carbonyl
     group is replaced by PO(OH)CH2"

( x i ) SEQUENCE DESCRIPTION: SEQ ID NO:9:

Pro His Pro Phe His Xaa Phe Val Tyr Lys
    1           5             10

( 2 ) INFORMATION FOR SEQ ID NO:10:

( i ) SEQUENCE CHARACTERISTICS:
   ( A ) LENGTH: 10 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Modified-site
   ( B ) LOCATION: 6
   ( D ) OTHER INFORMATION: /label=Xaa
     / note="Xaa is Leu whose carbonyl
     group is replaced by PO(OH)CH2"

( i x ) FEATURE:
   ( A ) NAME/KEY: Modified-site
   ( B ) LOCATION: 10
   ( D ) OTHER INFORMATION: /label=Xaa
     / note="Xaa is N-epsilon-t-BOC-Lys
     methyl ester"

( x i ) SEQUENCE DESCRIPTION: SEQ ID NO:10:

Arg Arg Pro Phe His Xaa Val Ile His Xaa
    1           5             10

( 2 ) INFORMATION FOR SEQ ID NO:11:

( i ) SEQUENCE CHARACTERISTICS:
   ( A ) LENGTH: 8 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Modified-site
   ( B ) LOCATION: 5
   ( D ) OTHER INFORMATION: /label=Xaa
     / note="Xaa is Leu whose carbonyl
     group is replaced by PO(OH)CH2"

( x i ) SEQUENCE DESCRIPTION: SEQ ID NO:11:

```
       His  Pro  Phe  His  Xaa  Leu  Val  Tyr
        1              5
```

( 2 ) INFORMATION FOR SEQ ID NO:12:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 5
        ( D ) OTHER INFORMATION: /label=Xaa
            / note="Xaa is Phe whose carbonyl
            group is replaced by PO(OH)CH2"

( x i ) SEQUENCE DESCRIPTION: SEQ ID NO:12:

```
       His  Pro  Phe  His  Xaa  Phe  Val  Tyr
        1              5
```

( 2 ) INFORMATION FOR SEQ ID NO:13:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 10
        ( D ) OTHER INFORMATION: /label=Xaa
            / note="Xaa is Leu whose carbonyl
            group is replaced by PO(OH)CH2"

( x i ) SEQUENCE DESCRIPTION: SEQ ID NO:13:

```
       Asp  Arg  Val  Tyr  Ile  His  Pro  Phe  His  Xaa  Val  Ile  His
        1              5                             10
```

( 2 ) INFORMATION FOR SEQ ID NO:14:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Xaa
            / note="Xaa is N-acetyl-Leu"

( i x ) FEATURE:
        ( A ) NAME/KEY: Modified-site
        ( B ) LOCATION: 3
        ( D ) OTHER INFORMATION: /label=Xaa
            / note="Xaa is Phe whose carbonyl
            group is replaced by PO(OH)CH2"

( x i ) SEQUENCE DESCRIPTION: SEQ ID NO:14:

```
       Xaa  Ser  Xaa  Met  Ala  Ile  Pro  Pro  Lys  Lys
        1              5                             10
```

( 2 ) INFORMATION FOR SEQ ID NO:15:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=Xaa
        / note="Xaa is N-acetyl-Val"

( i x ) FEATURE:
    ( A ) NAME/KEY: Modified-site
    ( B ) LOCATION: 3
    ( D ) OTHER INFORMATION: /label=Xaa
        / note="Xaa is Leu whose carbonyl
        group is replaced by PO(OH)CH2"

( x i ) SEQUENCE DESCRIPTION: SEQ ID NO:15:

Xaa  Val  Xaa  Ala  Leu
    1                       5

( 2 ) INFORMATION FOR SEQ ID NO:16:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Xaa
            / note="Xaa is N-3-methylbutanoyl-Val"

( i x ) FEATURE:
        ( A ) NAME/KEY: Modified-site
        ( B ) LOCATION: 3
        ( D ) OTHER INFORMATION: /label=Xaa
            / note="Xaa is Leu whose carbonyl
            group is replaced by PO(OH)CH2"

( i x ) FEATURE:
        ( A ) NAME/KEY: Modified-site
        ( B ) LOCATION: 4
        ( D ) OTHER INFORMATION: /label=Xaa
            / note="Xaa is Phe methyl ester"

( x i ) SEQUENCE DESCRIPTION: SEQ ID NO:16:

Xaa  Val  Xaa  Xaa
        1

( 2 ) INFORMATION FOR SEQ ID NO:17:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Xaa
            / note="Xaa is
            N-3- methylbutanoyl-Val"

( i x ) FEATURE:
    ( A ) NAME/KEY: Modified-site
    ( B ) LOCATION: 3
    ( D ) OTHER INFORMATION: /label=Xaa
        / note="Xaa is Leu whose carbonyl
        group is replaced by PO(OH)CH2"

( i x ) FEATURE:
    ( A ) NAME/KEY: Modified-site
    ( B ) LOCATION: 6
    ( D ) OTHER INFORMATION: /label=Xaa
        / note="Xaa is Ala methyl ester"

( x i ) SEQUENCE DESCRIPTION: SEQ ID NO:17:

```
Xaa  Val  Xaa  Phe  Ala  Xaa
 1                 5
```

( 2 ) INFORMATION FOR SEQ ID NO:18:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 3
        ( D ) OTHER INFORMATION: /label=Xaa
            / note="Xaa is homo-Arg"

( i x ) FEATURE:
        ( A ) NAME/KEY: Modified-site
        ( B ) LOCATION: 6
        ( D ) OTHER INFORMATION: /label=Xaa
            / note="Xaa is Leu whose carbonyl
            group is replaced by PO(OH)CH2"

( i x ) FEATURE:
        ( A ) NAME/KEY: Modified-site
        ( B ) LOCATION: 9
        ( D ) OTHER INFORMATION: /label=Xaa
            / note="Xaa is homo-Arg"

( i x ) FEATURE:
        ( A ) NAME/KEY: Modified-site
        ( B ) LOCATION: 10
        ( D ) OTHER INFORMATION: /label=Xaa
            / note="Xaa is homo-Arg"

( x i ) SEQUENCE DESCRIPTION: SEQ ID NO:18:

```
Leu  Val  Xaa  Val  Pro  Xaa  Val  Arg  Xaa  Xaa  Ser  Leu  Arg
 1                 5                           10

Gln  Leu  Ile
         15
```

( 2 ) INFORMATION FOR SEQ ID NO:19:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Xaa
            / note="Xaa is N-acetyl-Val"

( i x ) FEATURE:
        ( A ) NAME/KEY: Modified-site (B) LOCATION: 3
(D) OTHER INFORMATION: /label=Xaa
/ note="Xaa is Leu whose carbonyl
group is replaced by PO(OH)CH2"

(xi) SEQUENCE DESCRIPTION: SEQ ID NO:19:

Xaa Val Xaa Ala Ala Leu
1               5

(2) INFORMATION FOR SEQ ID NO:20:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 3
(D) OTHER INFORMATION: /label=Xaa
/ note="Xaa is Leu whose carbonyl
group is replaced by PO(OH)CH2"

(xi) SEQUENCE DESCRIPTION: SEQ ID NO:20:

Val Val Xaa Ala Ala Leu
1               5

(2) INFORMATION FOR SEQ ID NO:21:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /label=Xaa
/ note="Xaa is
N-3- methylbutanoyl-Val"

(ix) FEATURE:
(A) NAME/KEY: Modified-site
(B) LOCATION: 2
(D) OTHER INFORMATION: /label=Xaa
/ note="Xaa is Leu whose carbonyl
group is replaced by PO(OH)CH2"

(ix) FEATURE:
(A) NAME/KEY: Modified-site
(B) LOCATION: 4
(D) OTHER INFORMATION: /label=Xaa
/ note="Xaa is Ala isoamylamide"

(xi) SEQUENCE DESCRIPTION: SEQ ID NO:21:

Xaa Xaa Ala Xaa
1

(2) INFORMATION FOR SEQ ID NO:22:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide ( i x ) FEATURE:
  ( A ) NAME/KEY: Modified-site
  ( B ) LOCATION: 1
  ( D ) OTHER INFORMATION: /label=Xaa
    / note="Xaa is
    N-3- methylbutanoyl-Val"

( i x ) FEATURE:
  ( A ) NAME/KEY: Modified-site
  ( B ) LOCATION: 3
  ( D ) OTHER INFORMATION: /label=Xaa
    / note="Xaa is Leu whose carbonyl
    group is replaced by PO(OH)CH2"

( i x ) FEATURE:
  ( A ) NAME/KEY: Modified-site
  ( B ) LOCATION: 5
  ( D ) OTHER INFORMATION: /label=Xaa
    / note="Xaa is Ala ethyl ester"

( x i ) SEQUENCE DESCRIPTION: SEQ ID NO:22:

Xaa Val Xaa Ala Xaa
   1           5

( 2 ) INFORMATION FOR SEQ ID NO:23:

( i ) SEQUENCE CHARACTERISTICS:
  ( A ) LENGTH: 7 amino acids
  ( B ) TYPE: amino acid
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /label=Xaa
    / note="Xaa is N-acetyl-Ser"

( i x ) FEATURE:
  ( A ) NAME/KEY: Modified-site
  ( B ) LOCATION: 4
  ( D ) OTHER INFORMATION: /label=Xaa
    / note="Xaa is Phe whose carbonyl
    group is replaced by PO(OH)CH2"

( i x ) FEATURE:
  ( A ) NAME/KEY: Modified-site
  ( B ) LOCATION: 7
  ( D ) OTHER INFORMATION: /label=Xaa
    / note="Xaa is Val methyl ester"

( x i ) SEQUENCE DESCRIPTION: SEQ ID NO:23:

Xaa Leu Asn Xaa Pro Ile Xaa
   1          5

( 2 ) INFORMATION FOR SEQ ID NO:24:

( i ) SEQUENCE CHARACTERISTICS:
  ( A ) LENGTH: 7 amino acids
  ( B ) TYPE: amino acid
  ( D ) TOPOLOGY: linear ( i i ) MOLECULE TYPE: peptide ( i x ) FEATURE:
  ( A ) NAME/KEY: Modified-site
  ( B ) LOCATION: 1
  ( D ) OTHER INFORMATION: /label=Xaa
    / note="Xaa is N-valeryl-Ser"

( i x ) FEATURE:
  ( A ) NAME/KEY: Modified-site
  ( B ) LOCATION: 4
  ( D ) OTHER INFORMATION: /label=Xaa
    / note="Xaa is Phe whose carbonyl group is replaced by PO(OH)CH2"

( i x ) FEATURE:
    ( A ) NAME/KEY: Modified-site
    ( B ) LOCATION: 7
    ( D ) OTHER INFORMATION: /label=Xaa
        / note="Xaa is Val methyl ester"

( x i ) SEQUENCE DESCRIPTION: SEQ ID NO:24:

Xaa  Leu  Asn  Xaa  Pro  Ile  Xaa
     1                         5

( 2 ) INFORMATION FOR SEQ ID NO:25:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Xaa
            / note="Xaa is N-acetyl-Ser"

( i x ) FEATURE:
        ( A ) NAME/KEY: Modified-site
        ( B ) LOCATION: 2
        ( D ) OTHER INFORMATION: /label=Xaa
            / note="Xaa is D-Leu"

( i x ) FEATURE:
        ( A ) NAME/KEY: Modified-site
        ( B ) LOCATION: 4
        ( D ) OTHER INFORMATION: /label=Xaa
            / note="Xaa is Phe whose carbonyl
            group is replaced by PO(OH)CH2"

( i x ) FEATURE:
        ( A ) NAME/KEY: Modified-site
        ( B ) LOCATION: 7
        ( D ) OTHER INFORMATION: /label=Xaa
            / note="Xaa is Val methyl ester"

( x i ) SEQUENCE DESCRIPTION: SEQ ID NO:25:

Xaa  Xaa  Asn  Xaa  Pro  Ile  Xaa
     1                         5

( 2 ) INFORMATION FOR SEQ ID NO:26:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /label=Xaa
            / note="Xaa is N-acetyl-Ser"

( i x ) FEATURE:
        ( A ) NAME/KEY: Modified-site
        ( B ) LOCATION: 4
        ( D ) OTHER INFORMATION: /label=Xaa
            / note="Xaa is Tyr whose carbonyl
            group is replaced by PO(OH)CH2"

( i x ) FEATURE:
        ( A ) NAME/KEY: Modified-site
        ( B ) LOCATION: 7
        ( D ) OTHER INFORMATION: /label=Xaa / note="Xaa is Val methyl ester"

( x i ) SEQUENCE DESCRIPTION: SEQ ID NO:26:

Xaa Leu Asn Xaa Pro Ile Xaa
1                5

( 2 ) INFORMATION FOR SEQ ID NO:27:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=Xaa
          / note="Xaa is N-acetyl-Ser"

( i x ) FEATURE:
    ( A ) NAME/KEY: Modified-site
    ( B ) LOCATION: 4
    ( D ) OTHER INFORMATION: /label=Xaa
          / note="Xaa is Phe whose carbonyl
          group is replaced by PO(OH)CH2"

( i x ) FEATURE:
    ( A ) NAME/KEY: Modified-site
    ( B ) LOCATION: 5
    ( D ) OTHER INFORMATION: /label=Xaa
          / note="Xaa is piperidine-2(S)-carbonyl tert-butyl amide"

( x i ) SEQUENCE DESCRIPTION: SEQ ID NO:27:

Xaa Leu Asn Xaa Xaa
1              5

( 2 ) INFORMATION FOR SEQ ID NO:28:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /label=Xaa
          / note="Xaa is N-acetyl-Ser"

( i x ) FEATURE:
    ( A ) NAME/KEY: Modified-site
    ( B ) LOCATION: 4
    ( D ) OTHER INFORMATION: /label=Xaa
          / note="Xaa is Phe whose carbonyl
          group is replaced by PO(OH)CH2"

( i x ) FEATURE:
    ( A ) NAME/KEY: Modified-site
    ( B ) LOCATION: 5
    ( D ) OTHER INFORMATION: /label=Xaa
          / note="Xaa is (4aS,8aS)-decahydro-3(S)-isoquinoline
          carbonyl tert-butyl amide"

( x i ) SEQUENCE DESCRIPTION: SEQ ID NO:28:

Xaa Leu Asn Xaa Xaa
1              5

( 2 ) INFORMATION FOR SEQ ID NO:29:

( i ) SEQUENCE CHARACTERISTICS:

(A) LENGTH: 4 amino acids
(B) TYPE: amino acid
(D) TOPOLOGY: linear (i i) MOLECULE TYPE: peptide (i x) FEATURE:
    (A) NAME/KEY: Modified-site
    (B) LOCATION: 1
    (D) OTHER INFORMATION: /label=Xaa
        / note="Xaa is N-acetyl-Leu"

(i x) FEATURE:
    (A) NAME/KEY: Modified-site
    (B) LOCATION: 3
    (D) OTHER INFORMATION: /label=Xaa
        / note="Xaa is Phe whose carbonyl
        group is replaced by PO(OH)CH2"

(i x) FEATURE:
    (A) NAME/KEY: Modified-site
    (B) LOCATION: 4
    (D) OTHER INFORMATION: /label=Xaa
        / note="Xaa is piperidine-2(S)-carbonyl tert-butyl amide"

(x i) SEQUENCE DESCRIPTION: SEQ ID NO:29:

Xaa  Asn  Xaa  Xaa
    1

(2) INFORMATION FOR SEQ ID NO:30:

(i) SEQUENCE CHARACTERISTICS:
        (A) LENGTH: 4 amino acids
        (B) TYPE: amino acid
        (D) TOPOLOGY: linear (i i) MOLECULE TYPE: peptide (i x) FEATURE:
        (A) NAME/KEY: Modified-site
        (B) LOCATION: 1
        (D) OTHER INFORMATION: /label=Xaa
            / note="Xaa is N-acetyl-Leu"

(i x) FEATURE:
        (A) NAME/KEY: Modified-site
        (B) LOCATION: 3
        (D) OTHER INFORMATION: /label=Xaa
            / note="Xaa is Phe whose carbonyl
            group is replaced by PO(OH)CH2"

(i x) FEATURE:
        (A) NAME/KEY: Modified-site
        (B) LOCATION: 4
        (D) OTHER INFORMATION: /label=Xaa
            / note="Xaa is (4aS,8aS)-decahydro-3(S)-isoquinoline
            carbonyl tert-butyl amide"

(x i) SEQUENCE DESCRIPTION: SEQ ID NO:30:

Xaa  Asn  Xaa  Xaa
        1

(2) INFORMATION FOR SEQ ID NO:31:

(i) SEQUENCE CHARACTERISTICS:
        (A) LENGTH: 8 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Modified-site
        (B) LOCATION: 6
        (D) OTHER INFORMATION: /label=Xaa / note="Xaa is p-nitro-Phe"

( x i ) SEQUENCE DESCRIPTION: SEQ ID NO:31:

Lys  Pro  Ala  Glu  Phe  Xaa  Arg  Leu
     1                      5

( 2 ) INFORMATION FOR SEQ ID NO:32:

( i ) SEQUENCE CHARACTERISTICS:
      ( A ) LENGTH: 9 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 5
      ( D ) OTHER INFORMATION: /label=Xaa
          / note="Xaa is Nle"

( i x ) FEATURE:
      ( A ) NAME/KEY: Modified-site
      ( B ) LOCATION: 6
      ( D ) OTHER INFORMATION: /label=Xaa
          / note="Xaa is p-nitro-Phe"

( i x ) FEATURE:
      ( A ) NAME/KEY: Modified-site
      ( B ) LOCATION: 9
      ( D ) OTHER INFORMATION: /label=Xaa
          / note="Xaa is Nle amide"

( x i ) SEQUENCE DESCRIPTION: SEQ ID NO:32:

Lys  Ala  Arg  Val  Xaa  Xaa  Glu  Ala  Xaa
     1                      5